(12) United States Patent
Schlessinger et al.

(10) Patent No.: US 7,136,787 B2
(45) Date of Patent: Nov. 14, 2006

(54) GENERATION OF CONTINUOUS MATHEMATICAL MODEL FOR COMMON FEATURES OF A SUBJECT GROUP

(75) Inventors: Leonard Schlessinger, Pacific Palisades, CA (US); David Eddy, Aspen, CO (US)

(73) Assignee: Archimedes, Inc., San Francisco, CA (US)

(*) Notice: Subject to any disclaimer, the term of this patent is extended or adjusted under 35 U.S.C. 154(b) by 617 days.

(21) Appl. No.: 10/025,964

(22) Filed: Dec. 19, 2001

(65) Prior Publication Data

US 2005/0288910 A1 Dec. 29, 2005

(51) Int. Cl.
G06F 17/10 (2006.01)

(52) U.S. Cl. ............... 703/2; 382/132; 703/11; 707/1; 707/6; 707/7

(58) Field of Classification Search ............ 703/2, 703/11; 707/1, 6, 7; 382/132
See application file for complete search history.

(56) References Cited

U.S. PATENT DOCUMENTS

| | | | | |
|---|---|---|---|---|
| 5,327,893 A | * | 7/1994 | Savic | 600/454 |
| 5,657,255 A | | 8/1997 | Fink et al. | 364/578 |
| 5,808,918 A | | 9/1998 | Fink et al. | 364/578 |
| 5,930,154 A | | 7/1999 | Thalhammer-Reyero | 364/578 |
| 5,956,501 A | | 9/1999 | Brown | 395/500.32 |
| 6,003,029 A | * | 12/1999 | Agrawal et al. | 707/7 |
| 6,107,020 A | | 8/2000 | Skowron | 435/5 |
| 6,108,635 A | | 8/2000 | Herren et al. | 705/2 |
| 6,233,539 B1 | | 5/2001 | Brown | 703/11 |
| 6,766,283 B1 | * | 7/2004 | Goldman et al. | 703/2 |
| 6,862,561 B1 | | 3/2005 | Defranoux et al. | |

OTHER PUBLICATIONS

Andrew J. Newman, "Model Reduction Via the Karhunen-Loeve Expansion Part 1: An Exposition", Institute for Systems Research and Electrical Engineering Department, University of Maryland, pp. 1-19., Apr. 2, 1996.

S.P. Huang, et al., "Digital Simulation of Non-Gaussian Stationary Processes Using Karhunen-Loeve Expansion", 8th ASCE Specialty Conference on Probabilistic Mechanics and Structural Reliability, pp. 1-5, 2000.

International Search Report, application PCT/US 02/40582, international filing date Dec. 17, 2002, date Search Report mailed May 23, 2003.

(Continued)

Primary Examiner—Kamini Shah
Assistant Examiner—Herng-der Day
(74) Attorney, Agent, or Firm—Morrison & Foerster LLP

(57) ABSTRACT

A method for generating a continuous mathematical model of a feature common to subjects in a subject group includes selecting a sample data set from each subject in the subject group, selecting a set of expansion functions to be used in the representation of the sample data set, mathematically expanding each member of the sample data set in the form of a summation of results of multiplying each the expansion function in the set of expansion functions by a different mathematical parameter wherein the expanding determines a value for each of the different mathematical parameters, deriving a corresponding distribution function for each of the mathematical parameters, and generating the continuous mathematical model of the feature from the derived distribution functions and the expansion functions. In this way, the model is continuous in time, incorporates dependencies between various parameters, and allows for creation of simulated subjects having pertinent features occurring in real subjects.

53 Claims, 8 Drawing Sheets

OTHER PUBLICATIONS

Brown, Jonathan Betz et al., (2000) "The global diabetes model: user friendly version 3.0" *Diabetes Research and Clinical Practice,* 50 (Suppl. 3); S15-S46.

Brown, Jonathan Betz et al., (2000) "The Mt. Hood challenge: cross-testing two diabetes simulation models," *Diabetes Research and Clinical Practice,* 50 (Suppl. 3); S57-S64.

Brown, Jonathan Betz et al., (Jun. 2000) "Relative Effectiveness of Blood Pressure vs. Glycemic Control in Type 2 Diabetes: The Global Diabetes Model," 60th Annual Meeting and Scientific Sessions of the American Diabetes Association, San Antonia, Texas, Jun. 10-13, Text of Poster presented at.

* cited by examiner

GENERATION OF CONTINUOUS MATHEMATICAL MODEL FOR COMMON FEATURES OF A SUBJECT GROUP

FIELD OF THE INVENTION

The present invention is generally directed to the generation of mathematical models and more particularly to the generation of continuous mathematical models of a feature or features common to subjects in a subject group.

BACKGROUND OF THE INVENTION

Mathematical modeling is well known in the art. Presently, mathematical models are in widespread use in nearly all forms of technologies such as in computer hardware and software and as an aide in the optimizing and improving of practically every development and manufacturing effort. As a result, mathematical models play an integral role in most technologies in use today.

These mathematical models have been developed and applied to a wide variety of technologies depending upon the intended need at the implementation site. One useful application of mathematical models today is in the field of health care. Delivering high quality health care efficiently generally requires making a large number of decisions as to which treatments to administer to which patients at what times and using what processes. While every conceivable alternative may be tried in an experimental setting to empirically determine the best possible approach, as a practical matter such a scenario is often impossible to carry out. Prohibitive factors such as the large number and combinations of interventions, the required long follow up times, the difficulty of collecting data and of getting patients and practitioners to comply with experimental designs, and the financial costs of the experiment, among other factors, all contribute to render an experimental approach impractical. Therefore it is highly desirable to use mathematical models in the development and implementations of high quality health care.

While offering a significant advantage over the experimental approach, the current usage of mathematical models in health care is not without shortcomings. Presently, mathematical models are generally used to address very narrow questions, such as the frequency of a particular screening test. More importantly, these models are discrete in scope and lack inclusion of any time factor at all, or include only one time period or a series of fixed time periods. In addition, these models generally do not include intervention factors or events that occur in the intervals between the fixed periods of other models, nor do they incorporate the dependencies between various parameters of the model, such as dependencies between biological features of a subject and its disease afflictions.

This invention generates a mathematical model of a feature common to subjects that is continuous in time, incorporates dependencies between the various parameters of the model, enables comparison of interventions that affect multiple features and allows for creation of simulated subjects that have all the pertinent features occurring in real subjects.

SUMMARY OF THE INVENTION

In one aspect of the invention, a continuous mathematical model of a feature common to subjects in a subject group is generated. This is accomplished by selecting a sample data set from each subject in the subject group. A set of expansion functions is selected to be used in the representation of the sample data set. A mathematical expansion is performed on each member of the sample data set in the form of a summation of all of the results of the mathematical operations in which each expansion function in the set of expansion functions is multiplied by a different mathematical parameter. The mathematical expansion also determines a value for each of the different mathematical parameters for each subject in the subject group. A corresponding distribution function is derived for each of the mathematical parameters and a continuous mathematical model of the feature is generated from the derived distribution functions and the expansion functions.

In another aspect of the invention a continuous mathematical model of a plurality of features common to subjects in a subject group is generated. This is accomplished by selecting two or more sample data sets from each subject in the subject group wherein each sample data set relates to a different feature. A set of expansion functions is selected to be used in the representation of each of the sample data set. A mathematical expansion is performed on each member of each sample data set in the form of a summation of all of the results of the mathematical operations in which each expansion function in the set of expansion functions of the data set is multiplied by a different mathematical parameter. The mathematical expansion also determines a value for each of the mathematical parameters for each subject in the subject group. A corresponding distribution function is derived for each of the mathematical parameters and a continuous mathematical model is generated for each of the selected features from the derived distribution functions and the expansion functions of that selected feature. The generated mathematical models of all of the features are correlated and, based on that correlation and the derived corresponding distribution functions, a continuous mathematical model for all the features is generated.

BRIEF DESCRIPTION OF THE DRAWINGS

The accompanying drawings, which are incorporated into and constitute a part of this specification, illustrate one or more exemplary embodiments of the present invention, and together with the detailed description, serve to explain the principles and exemplary implementations of the invention.

In the drawing.

DETAILED DESCRIPTION OF THE INVENTION

Figure 1:
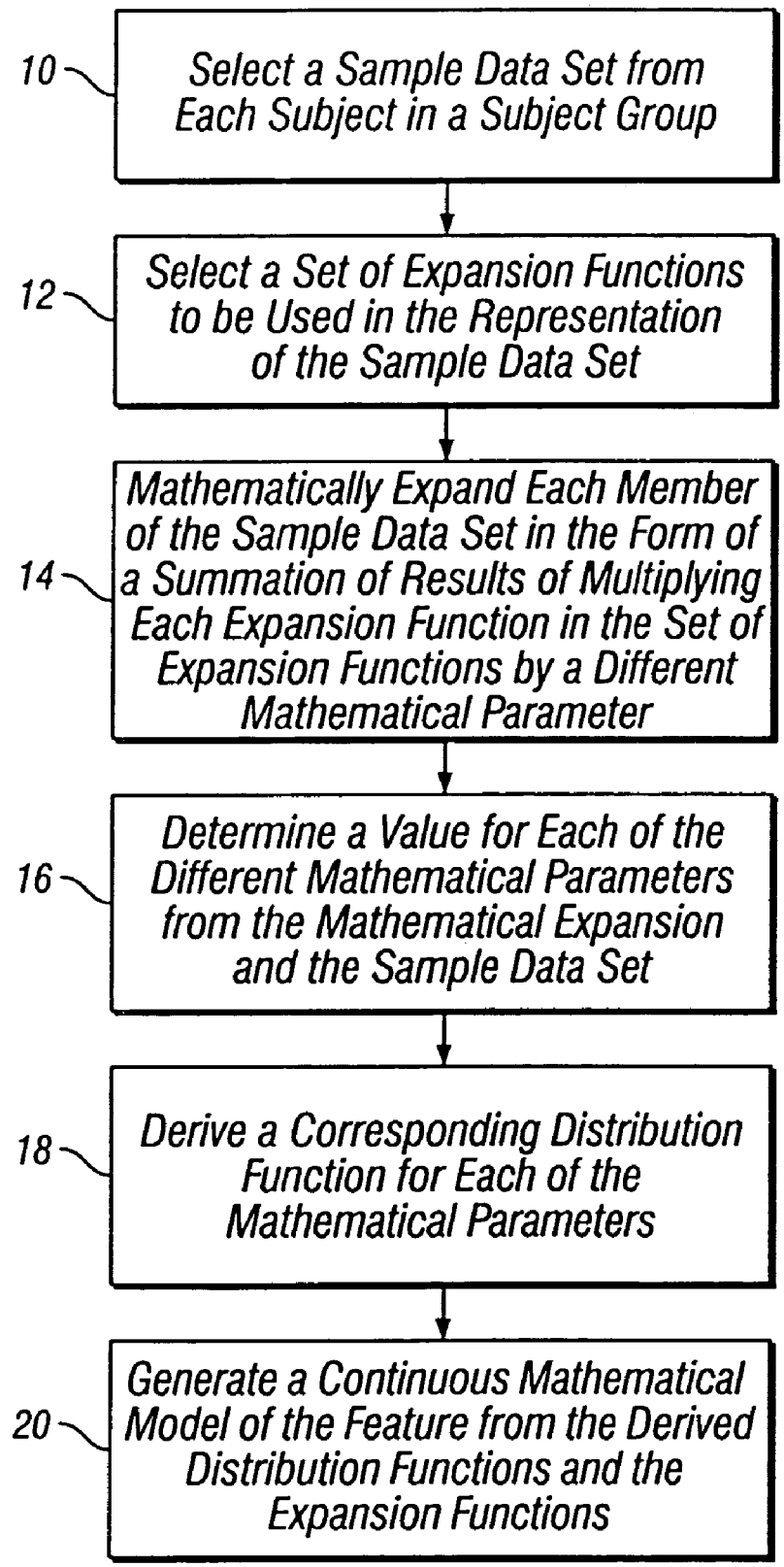
FIG. 1 is a flow diagram for generating a continuous mathematical model in accordance with one embodiment of the invention.

Various exemplary embodiments of the invention are described herein in the context of generating a continuous mathematical model of a feature common to subjects in a subject group. Those of ordinary skill in the art will realize that the following detailed description of the present invention is illustrative only and is not intended to be in any way limiting. Other embodiments of the invention will readily suggest themselves to such skilled persons having the benefit of this disclosure. Reference will now be made in detail to exemplary implementations of the present invention as illustrated in the accompanying drawings. The same reference indicators will be used throughout the drawings and the following detailed descriptions to refer to the same or like parts.

In the interest of clarity, not all of the routine features of the exemplary implementations described herein are shown and described. It will of course, be appreciated that in the development of any such actual implementation, numerous implementation specific decisions must be made in order to achieve the developer's specific goals, such as compliance with application and business related constraints, and that these specific goals will vary from one implementation to another and from one developer to another. Moreover, it will be appreciated that such a development effort might be complex and time consuming, but would nevertheless be a routine undertaking of engineering for those of ordinary skill in the art having the benefit of this disclosure.

Referring now more particularly to the Drawings, the present invention is directed to generating a continuous mathematical model of a feature common to subjects in a subject group. As shown in the flow diagram of FIG. 1, a method for generating a continuous mathematical model of a feature such as blood pressure in a group of humans starts at block 10 where a sample data set from each subject in the subject group is selected. Next, at block 12, a set of expansion functions to be used in the representation of the sample data set is also selected. At block 14, the selections made in blocks 10 and 12 are used to mathematically expand each member of the sample data set in the form of a summation of the results of multiplying each of the expansion functions in the set of expansion functions by a different mathematical parameter. Next, at block 16, a value for each of the different mathematical parameters is determined from the mathematical expansion of block 14. Next, at block 18, a corresponding distribution function for each of the mathematical parameters is derived based on the values determined in block 16. Finally, at block 20, a continuous mathematical model of the feature is generated from the derived distribution functions of block 18 and the expansion functions of block 12. The details and purpose of operations performed in each block in FIG. 1 will now be explained in greater detail in conjunction with the accompanying figures.

Generally, mathematical simulation models are distinguished from other types of conceptual models by their inclusion of simulated objects, such as subjects, that correspond to real objects on a one-to-one basis. These simulations vary greatly in their scope such as in breadth, depth, and realism, and therefore require a very broad, deep and realistic model that could be used to address the full range of pertinent issues, such as clinical, administrative, and financial decisions in the health care context, at the level of detail at which real decisions can be made. Development of such a model requires creating a population of simulated individuals who experience all of the important events that occur in real subjects, and who respond to interventions in the same way as real subjects. In health care, for example, such developments require modeling the essential aspects of human anatomy, physiology, pathology, and response to medical treatment. Because timing is also an essential element of the occurrence, manifestation, progression, management, and outcome of disease, the model must also be continuous, rather than discontinuous.

To better demonstrate the various features and aspects of the present invention, a health-based model is consistently used throughout the specification as an exemplary environment. It should be noted however, that the invention disclosed herein is not limited to health care and its formulation and equations are general and can be applied to virtually any environment involving humans or non-humans, living or mechanical systems and the like. For example, this approach could be used to model animal or plant responses, or even complex mechanical, electromechanical or electronic systems.

In a health care environment, the physiology of a subject is characterized by "features," which correspond to a wide variety of anatomic and biologic variables. Examples of features which may be modeled include, but are not limited to: blood pressure, cholesterol levels (i.e., high-density lipoprotein [HDL] and low-density lipoprotein [LDL]), bone mineral density, patency of a coronary artery, electrical potentials of the heart (as recorded on an electrocardiogram), contractility of myocardium, cardiac output, visual acuity, and serum potassium level. A feature can be continuously observable (e.g., a rash), intermittently observable through tests (e.g., diameter of a coronary artery), or not directly observable except through resultant events (e.g, "spread" of a cancer).

The "trajectory" of a feature, defined as the changes in a feature over time, in a particular subject can be affected by the subject's characteristics, behaviors and other features, often called "risk factors." For example, the occlusion of a coronary artery can be affected by an individual's family history (genetics), sex, age, use of tobacco, blood pressure, LDL cholesterol level, and many other risk factors. If no interventions are applied to change it, the trajectory of a feature is called its "natural trajectory" or, in the medical vernacular, its "natural history."

A "disease" is generally defined as an occurrence when one or more features are considered "abnormal", however, because concepts of abnormality can change, definitions of diseases can change. Furthermore many definitions of diseases are "man made" and gross simplifications of the underlying physiology, and many diseases have different definitions put forth by different experts. For these reasons, it is important to model the underlying features rather than whatever definition of a disease is current. Additionally, because the definition of a disease often omits important behaviors and risk factors, it is sometimes more appropriate to think more broadly of "health conditions."

For many diseases, there are "health interventions" which can change the value of one or more features, the rate of progression of one or more features, or both value and rate of progression. Interventions may affect features either indirectly (by changing risk factors, e.g., smoking) or directly (by changing the feature itself). Health interventions which have direct effects can change either the value of a feature (e.g., performing bypass surgery to open an occluded coronary artery) or the rate of change of a feature (e.g., lowering cholesterol to slow the rate of occlusion).

Accuracy is also a critical feature of any model. For models to be considered sufficiently accurate to be applied in the decision making process, the models must meet the following criteria. First, they must cause the events in the simulated population to statistically match the events observed in a real population. Second, they must cause the effects of treatment in the simulated population to statistically match the effects seen in real populations. This statistical matching arises because of the type of data available. In some cases, there are person-specific data on the values of a feature and the events it causes. In such cases, the models need to be able to reproduce those data for every individual, every value of the feature, and every event observed. In other cases, the data are aggregated across the population and are statistical in nature. For example, there may be data on the age specific incidence rates of breast cancer in a population, or the distribution of ages at which heart attack occurs in a population.

In these cases, as described above, statistical matching mandates that the statistics that describe the occurrence of events in the simulated population must match the statistics that describe the occurrence of events in the real population for every event observed. For example, the age specific incidence rates of breast cancer in the simulated population must be the same as in the real population, and both mean and variance of age distribution at which heart attacks occur in the simulated population must be the same as in the real population. Similarly, if a clinical trial of a treatment in a real population showed a particular effect on the occurrence of certain outcomes after a certain number of years, "statistical matching" would require that when the same treatment is given to a simulated population that is constructed to have the same characteristics as the real population, it must show the same effects on the outcomes after the same length of follow up.

The accuracy of a statistical match depends on the size of the simulated population. Since, as in real trials, simulated trials are affected by sample size, statistical matching requires that simulated results match real results within appropriate confidence intervals, and that as the size of the simulation increases the simulated results will converge on the real results.

Features that define important diseases can also be represented by statistical models. These models for the features depend on the number of features, the number of events and the available data. In its simplest form, the model is of a single feature of a person, and there are person specific data available on the values of the feature at a series of times. For an example, if a selected organ is the heart, then a part of the organ is a coronary artery, the feature can be the degree of occlusion of the artery, and an event associated with the feature can be a heart attack.

For each subject it is desirable to define a function that describes the natural progression or trajectory of the feature over time, such as from birth to death, where "natural" means the trajectory of the feature in the absence of any special interventions from the health care system. Other equations can then be used to simulate the effects of interventions.

For example, if a particular subject is indexed by k, then the trajectory of a particular feature for the $k^{th}$ subject can be modeled $F^k(t)$, where t is the time since the subject's birth (age). Because interventions can change either the value of a feature or the rate of change of a feature, a differential equation is used for $F^k(t)$. The general form of the differential equation for each subject is $$\frac{dF^k(t)}{dt} = R^k(t), \qquad \text{Eq. (1)}$$

where $F^k(t)$ is the value of the feature at time t for the $k^{th}$ subject, and $R^k(t)$ is the rate at which the value of the feature is changing at time t (the derivative). Either $F^k(t)$ or $R^k(t)$ determines the natural trajectory for the $k^{th}$ subject, and either $F^k(t)$ or $R^k(t)$ can be determined from the other. For simplicity of description, the focus is on the value of the feature, $F^k(t)$, with the understanding that the rate of change of the feature, $R^k(t)$, can always be derived from $F^k(t)$ by equation (1).

In accordance with the present invention, a set of trajectories are created for a population of simulated subjects. The created trajectories are designed to statistically match the trajectories of a population of real subjects. As shown in FIG. 1, at first, in block 10, a sample data set from each subject in the subject group is selected.

Figure 2:
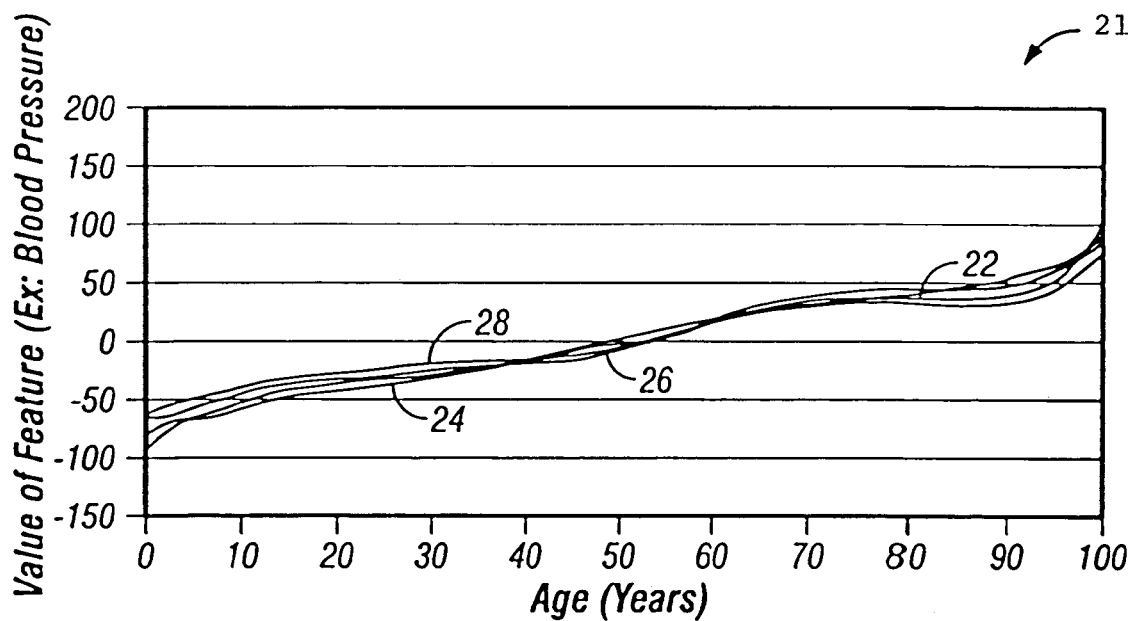
FIG. 2 is a diagram illustrating a sample space with various trajectories of a feature common to real subjects in accordance with one embodiment of the invention.
Figure 3:
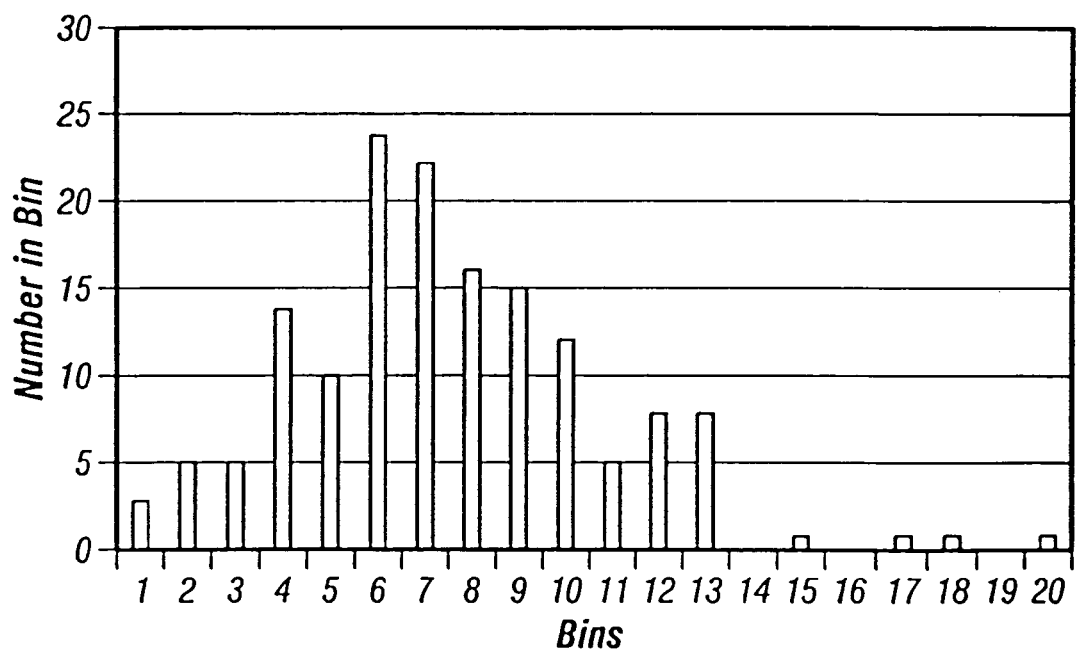
FIGS. 3, 4, 5, 6, 7, 8, 9A, 9B and 9C illustrate exemplary probability distribution diagrams in histogram form used to generate a continuous mathematical model in accordance with an embodiment of the invention.
Figure 4:
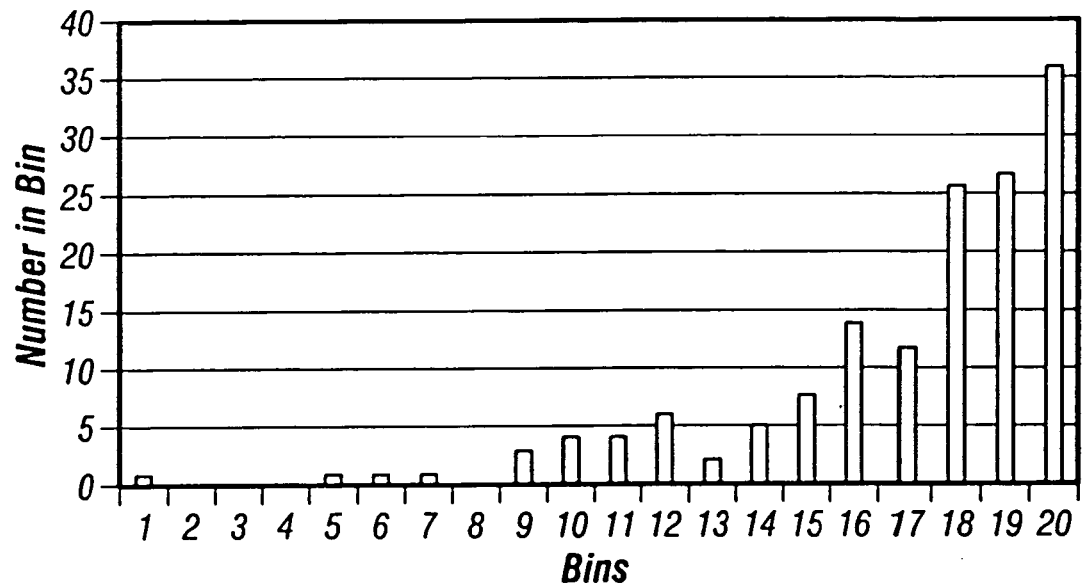
Figure 5:
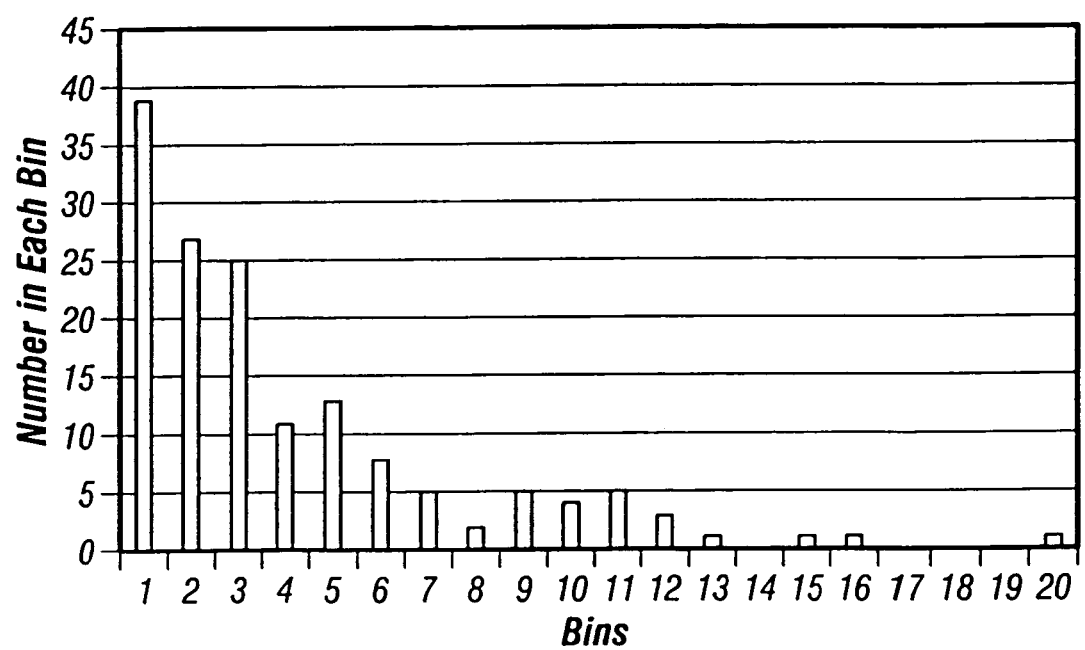
Figure 6:
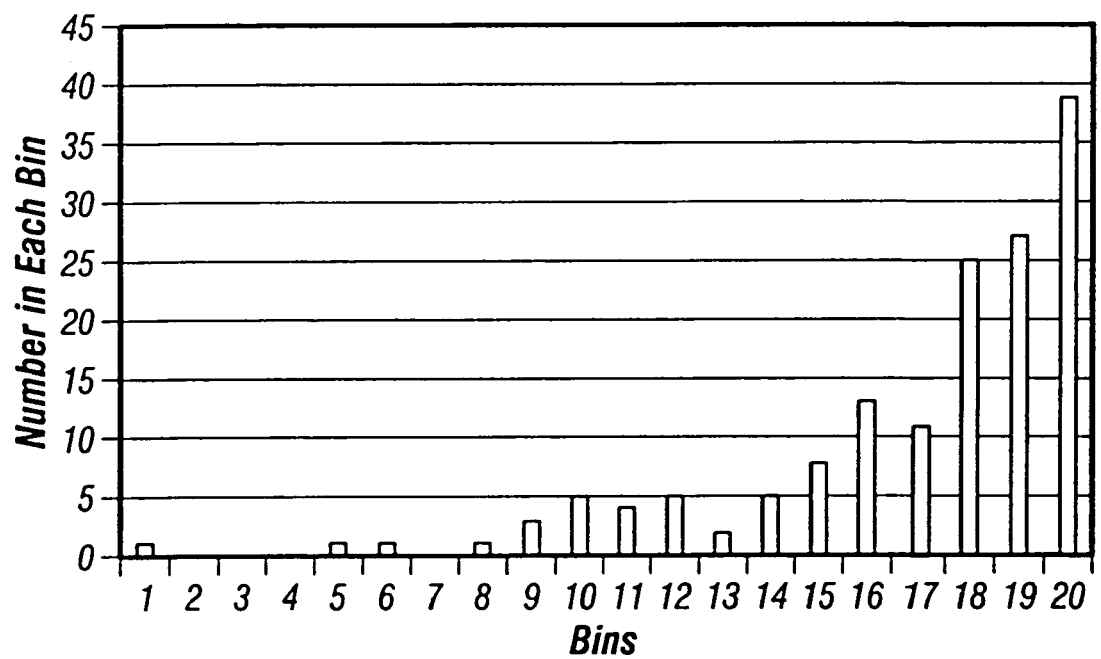
Figure 7:
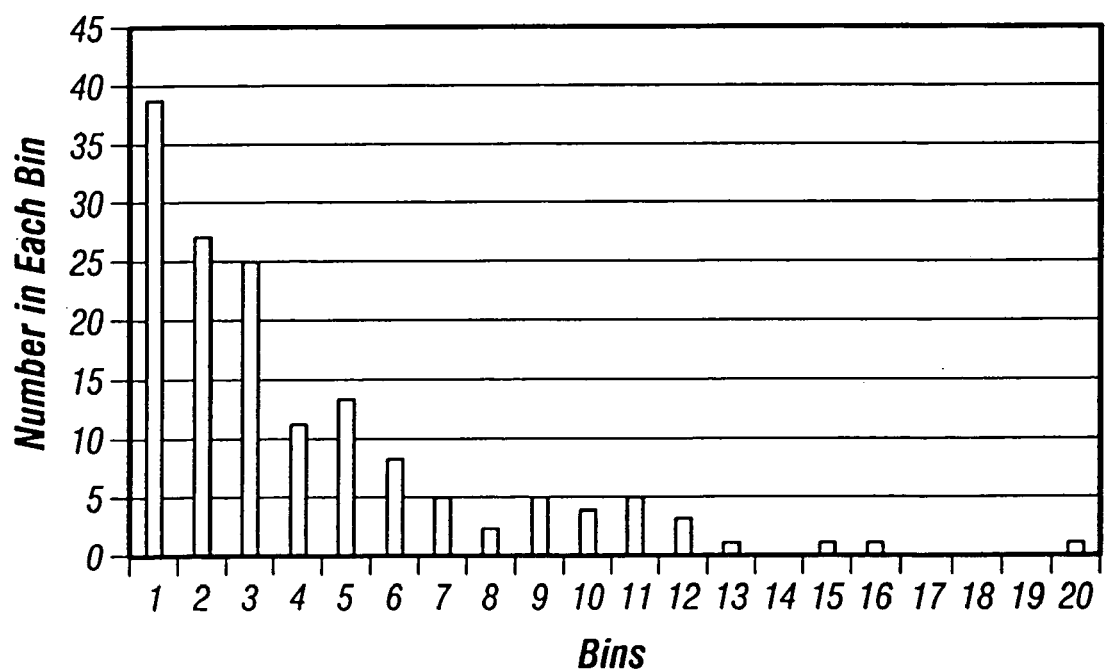
Figure 8:
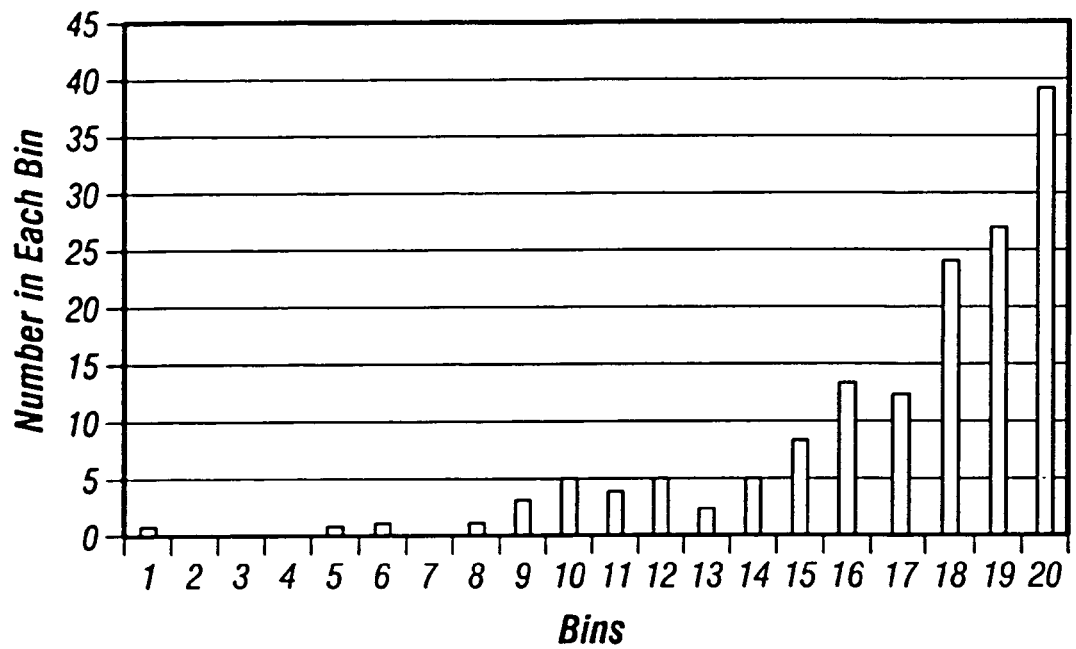

FIG. 2 is a diagram illustrating the various trajectories of a feature, such as blood pressure, common to real subjects in a subject group in sample space 21. For simplicity, the trajectories for only four subjects 22, 24, 26 and 28 are enumerated herein, although any number of real subjects can be used. Each trajectory on the sample space 21 represents a sample data set on the same feature of each subject, such as the subject's blood pressure level, at a specific age. Additionally, the trajectories of real subjects are considered a random (stochastic) process parameterized by age, although as described below, the random process can be conditional on risk factors and other features. The sample space 21 for a particular feature is the collection of the one trajectory for each person. For simplicity, the sample space 21 is mathematically denoted as "$\Omega$" throughout the equations in the specifications, with elements $\omega = \{\omega_1, \omega_2, \omega_3 \ldots\}$, where $\omega_k$ specifies the trajectory of the feature of a particular person, such as trajectory 22 in FIG. 2. The random process for the trajectories is designated by upper case letters set in boldface font and is notated as having explicit dependence on $\omega$, that is, $F(\omega, t)$. Each function in equation (1) is a realization of the stochastic process insofar as $F^k(t)=F(\omega_k,t)$, where $\omega_k$ is the trajectory of the $k^{th}$ person in the set $\omega$.

Returning to FIG. 1, at block 12 a set of expansion functions are selected. As described below and in greater detail, these expansion functions are used in the representation of the sample data sets.

Next, in block 14, the selections made in blocks 10 and 12 are used to mathematically expand each member of the sample data set in the form of a summation of the results of multiplying each of the expansion functions in the set of expansion functions by a different mathematical parameter, such as the weighted coefficients. In an exemplary embodiment, the total number of parameters cannot exceed the total number of sample data points used in a subject data set. In its simplest form, only one parameter is used. Next, at block 16, a mathematical expansion is performed on the selected data sets to determine the values for each selected parameter. There are many ways well known to those skilled in the art to estimate the specific values for the mathematical parameters, depending on how the expansion functions are chosen. In an exemplary embodiment, the method used is one that is guaranteed to mathematically converge, such as a Fourier expansion.

Using a Fourier expansion involves expanding $F(\omega,t)$ (or any function of $F(\omega,t)$, such as the log of the odds ratio of $F(\omega,t)$, a logit transform) in a Fourier-type series. Each term of the series includes two parts: an age dependent, deterministic (nonrandom) "basis" expansion function (denoted as $P_j(t)$ for the $j^{th}$ term in the expansion), multiplied by a mathematical parameter, also called a coefficient, (denoted by a lower case letter) which is an age independent random variable, $f_j(\omega)$. The basis functions $P_j(t)$ could be any set of functions. Some examples include: a polynomial series, i.e., $t^j$, the $j^{th}$ Legendre or Laguerre polynomial, or a Fourier series, i.e., $\sin(jt/T)$.

When the basis functions are chosen to be orthonormal over the range of ages of interest, then the expansion is called a Karhunen-Loeve (K-L) decomposition. Because the theory of K-L decompositions is reasonably well developed and because the K-L decomposition has several well known advantages, there are good reasons to choose the $P_j(t)$ to be orthonormal. The Legendre, Laguerre, and Fourier functions are examples of such orthonormal functions.

Whichever basis function is chosen, it is to be the same for every subject in the model. The coefficients $f_j(\omega)$, however, are random variables and are to be different for each subject. Choice of basis functions thus affects the coefficients calculated and the rate of convergence for the series (i.e., number of terms needed to fit the data) but will not prevent the method from working.

Thus, in general, the mathematical expansion will have the form of:

$$F(\omega, t) = \sum_{j=0}^{\infty} f_j(\omega) P_j(t). \qquad \text{Eq. (2)}$$

Samples of the distributions for the coefficients $f_j(\omega)$ are now estimated. In practice, the summation in equation (2) is truncated to a finite number of terms, J+1. This number is related to (but not greater than) the number of events observed for each subject. The method for estimating the $f_j(\omega)$ depends on the available data. In a desirable case, there are subject specific data that provide a series of values of the feature at specified times for a large number of subjects. For example, there might be a series of measurements of intraocular pressures for a group of subjects. In addition there is no requirement that the measurements for each person be taken at the same times.

The function describing the trajectory for the $k^{th}$ real person is approximated by a finite sum, $$F^k(t) \approx \sum_{j=0}^{J} f_j^k P_j(t), \qquad \text{Eq. (3)}$$

where $f_j^k$ are the coefficients determined to fit the data observed for the subject. The $f_j^k$ coefficients are the samples that will be used to estimate the distribution of the coefficients $f_j(\omega)$. There are many different ways that can be used to estimate the $f_j^k$ from the data, and for simplicity only three methods are described herein: (a) the method requiring the expansion in equation (3) to pass through all of the observed points, (b) the method of least squares, and (c) the method using the orthonormal properties of $P_j(t)$.

Using the first method envisions that for each person there are J+1 observations. This will lead to J+1 equations with J+1 unknowns. This linear system of equations can be solved for the $f_j^k$ coefficients using standard methods.

The second method of determining the $f_j^k$ coefficients is by least squares. This method is most desirable to use when the number of terms is less than the number of observations for each person. For example, if there are M observations that can be used to determine coefficients for the J+1 terms, where J<M, the $f_j^k$ coefficients can be determined by minimizing the sum of the squares of the differences between the value of the function and the value of the expansion on the right hand side of equation (3) at all of the M points. The expression to be minimized for this method is $$\sum_{m=1}^{m=M} \left( F^k(t_m) - \sum_{j=0}^{j=J} f_j^k P_j(t_m) \right)^2.$$

Taking the derivative of this equation with respect to each $f_j^k$ (j=0 to J) and setting this derivative to zero produces a set of linear equations which determine the $f_j^k$.

The third way to determine the $f_j^k$ makes use of the orthonormal properties of the $P_j(t)$. Multiplying both sides of equation (3) by $P_j(t)*W(t)$ (where W(t) is the weight for that orthonormal function) and using the orthogonality property, directly yields the following expression for $f_j^k$:

$$f_j^k = \int F^k(t) * P_j(t) * W(t) dt \qquad \text{Eq. (4)}.$$

The observed points are used to approximate the integral. As before, there must be at least J+1 observations. The coefficients determined in this way will minimize the integral of the square of the difference between the right and left sides of Eq. (3). That is, the coefficients will minimize $$\int dt \left( F^k(t) - \sum_{j=0}^{j=J} f_j^k P_j(t) \right)^2 W(t).$$

The underlying theory for this type of expansion are well known functional analysis techniques. One advantage of using this method is that the power of the theory of functional analysis can be applied to the estimation procedure. Moreover, many properties of the K-L decomposition require the use of this type of expansion.

For any set of basis functions chosen initially, any of these three methods can be used to find values of the coefficients which cause each person's trajectory to fit the data.

In another exemplary embodiment, Hybrid expansion is used in block 14 of FIG. 1. The Hybrid expansion is more closely related to the familiar regression techniques used to analyze health data but unlike the Fourier expansion, the Hybrid expansion is not guaranteed to converge.

Hybrid expansion is employed in the cases where the use of a nonstandard functions may be helpful as part of the set of basis functions. For instance, when a feature may reasonably be believed to depend strongly on one or more other features, a natural tendency may be to try to incorporate that dependency explicitly into the basis functions. Specifically, for example, occlusion of the coronary artery ($F_1$) is known to depend on both blood pressure ($F_2$) and cholesterol level ($F_3$), among other things. These features can be included in the expansion for $F_1$ as follows:

(a) As described above for a Fourier expansion, the set of basis functions is $P_j(t)$. However, instead of choosing the $P_j(t)$ orthonormal, the $P_0(t)$ represents blood pressure level for the subject, and $P_1(t)$ represent total cholesterol level for that subject. Additional basis functions could be chosen to address dependencies or other relations between features. For example, $P_2(t)$ can represents the product of blood pressure level and total cholesterol level and $P_3(t)$ can represents the product of three values: t, blood pressure level, and cholesterol level. As in the Fourier expansion, the remaining basis functions would be the orthonormal set.

(b) After the first few basis functions are chosen to include other features, the remainder of the analysis can proceed as for the Fourier expansion except that Eq. (4) cannot be used to determine the coefficients (i.e., because the full set of basis functions is no longer orthonormal). The other equations will still apply however. For example, the covariance matrix can still be diagonalized to obtain a new set of basis functions having the desired properties. It should be noted, however, that the first few basis functions will be different for every subject because the functions describe the progression of a particular feature for a particular subject.

This type of Hybrid expansion is related to the expansions traditionally used in regression analyses. The independent variables in a regression equation correspond to the basis functions in the mathematical model of the present invention, and the coefficients also correspond to the coefficients used in the model of the present invention.

The hybrid method has several advantages: (a) it is intuitively appealing; (b) it corresponds to regression models, which are familiar; and (c) it can determine how important is the dependence of one feature on another (e.g., importance of blood pressure level in determining progression of coronary artery occlusion). Moreover, the hybrid method can converge even faster than can the conventional method.

After the determination of the values of the coefficients using a mathematical expansion is performed in blocks 14 and 16 of FIG. 1, the flow proceeds to block 18 where a probability distribution is generated from the determined values of the coefficients using various implementations of the well known Maximum Likelihood technique.

At this point new values for the trajectories can be generated by the continuous mathematical model to create new simulated subject which can be used to explore outcomes and effects of interventions in the new simulated group.

The following Example 1 is provided to further illustrate the above-described workings of the present invention:

FIG. 2 shows a set of trajectories selected from a large subject group. In this example, K trajectories are selected and though they are not all shown, they all adhere to the general form of those enumerated as 22, 24, 26 and 28. Each of these trajectories is one of the $F^k(t)$ functions described above. Next, each trajectory is fitted into a series having the mathematical form of $$F^k(t) \approx \sum_{j=0}^{J} f_j^k P_j(t).$$

In this example, a function $P_j(t)=(t/50)^j$ is used as the expansion function and J is set to 6, both for illustrative purposes only. Thus, with J equal to 6, there are seven terms (0–6) in the series, resulting in a large set of $f_j^k$, as there are seven values of j for each value of k and there are K individuals or values of k in the sample. Thus, there are values of $f_j^k$ for each value of j. These values are the samples of that are used to determine the distribution of each $f_j$. Using these samples, distribution of the $f_j^k$ is obtained using various implementations of the well known Maximum Likelihood technique. The samples of the distribution for each of the seven $f_j$, $f_0$ to $f_6$ are shown histogrammatically in each of FIGS. 3–9A, respectively. FIGS. 3–9A, thus show the number of samples of $f_j^k$ in each bin where each $f_j$ with the following range (along the horizontal axis) is divided from the smallest to the largest value of the samples of $f_j^k$ into 20 bins: $f_0$ ranges from −28.4 to 54.1, $f_1$ ranges from −1059.6 to 224.1, $f_2$ ranges from 1107.3 to 5278.1, $f_3$ ranges from 1055.7 to 2214.7.1, $f_4$ range from 2076 to 9895, $f_5$ ranges from −4353.9 to 913.6, and $f_6$ ranges from −152.3 to 725.6.

Figure 10:
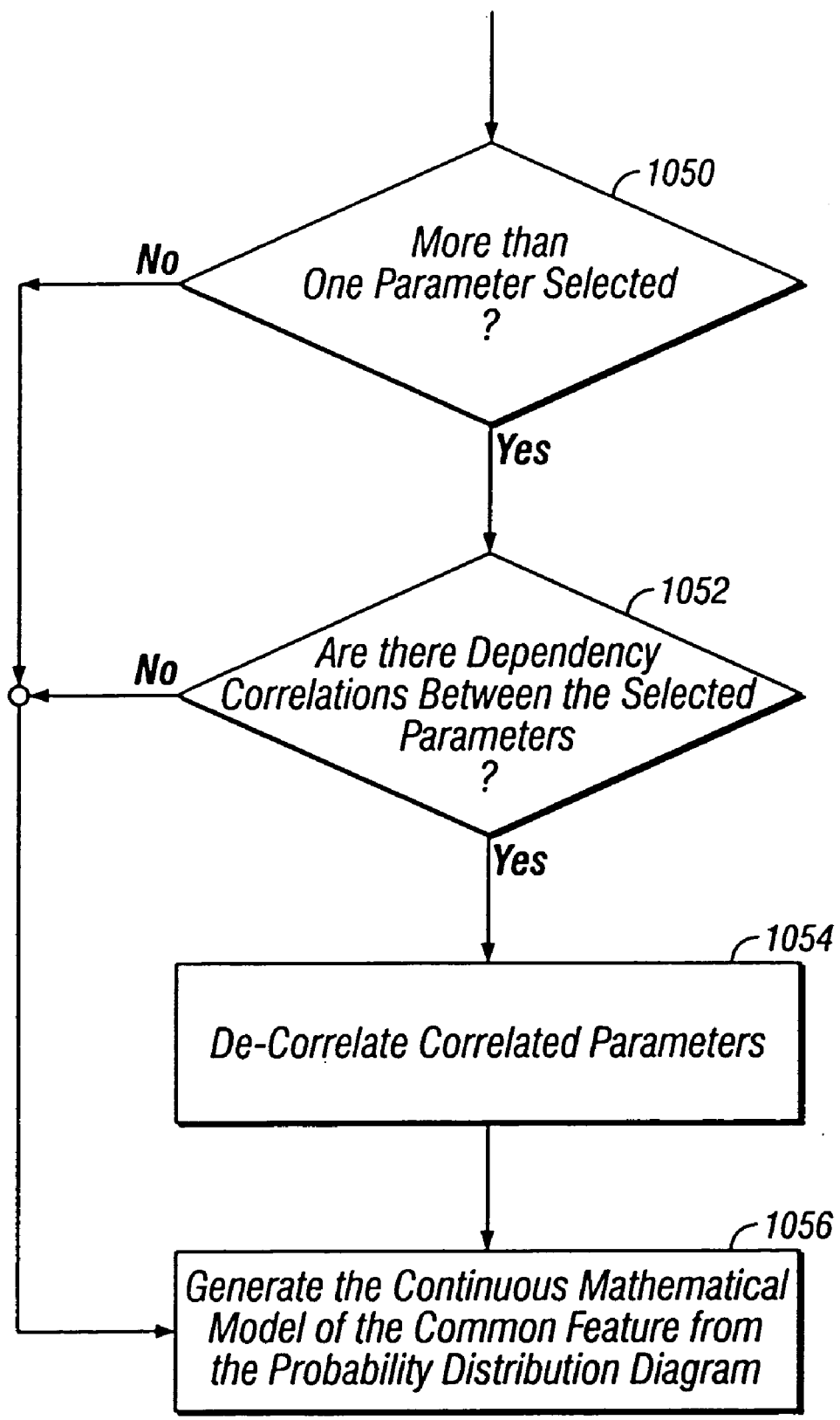
FIG. 10 is a process flow diagram illustrating a method for resolution of dependencies of the mathematical parameters in accordance with one embodiment of the invention.

Other contingencies in generating the mathematical model of the present invention will now be discussed in greater detail. FIG. 10 is a flow diagram illustrating the resolution of dependencies of the selected parameters $f_j(\omega)$ prior to generating the continuous mathematical model. Generally, if $f_j(\omega)$ represent independent random variables, a particular subject could be created by drawing values for each of the j random variables $f_j(\omega)$ and then using Eq. (3) to calculate a particular simulated trajectory. As shown in decision block 1050, if only one parameter is selected, the independence of the coefficients is automatically guaranteed and the flow proceeds to block 1056 for generation of the continuous mathematical model of the common feature from the probability distribution diagram.

If more than one coefficient is selected, then the flow proceeds to the decision block 1052 where a determination is made as to the independence of the coefficients $f_j(\omega)$. If the $f_j(\omega)$ values are independent, then their covariance is zero. First, the distributions of each coefficient is transformed by subtracting out the mean of the individual values of the coefficient. For notational simplicity the mean of a coefficient is represented with angle brackets throughout the disclosure. Thus, for the $j^{th}$ coefficient $$\langle f_j \rangle = \frac{1}{K} \sum_{k=1}^{K} f_j^k, \quad \text{Eq. (5)}$$

where K is the total number of individuals for which data exist. Then for the $k^{th}$ individual, subtracting out the means from the coefficients in Eq. (3) yields $$F^k(t) = \left( \sum_{j=0}^{J} (f_j^k - \langle f_j \rangle) P_j(t) \right) + \left( \sum_{j=0}^{J} \langle f_j \rangle P_j(t) \right). \quad \text{Eq. (6)}$$

The coefficient of the first term on the right is the original coefficient with the mean subtracted out. The last term on the right is required to maintain the equation, and can be thought of as the average trajectory—the basis functions weighted by the average values of the coefficients, which can be represented as <F(t)>—that is, $$\langle F(t) \rangle = \sum_{j=0}^{J} \langle f_j \rangle P_j(t). \quad \text{Eq. (7)}$$

We can let q represent the new coefficient; that is, $$q_j^k = f_j^k - \langle f_j \rangle \quad \text{Eq. (8).}$$

This results in a new equation for the trajectory of the feature. Substituting Eq. (7) and Eq.(8) in Eq. (6) yields:

$$F^k(t) = \sum_{j=0}^{J} q_j^k P_j(t) + \langle F(t) \rangle. \quad \text{Eq. (9)}$$

Now the covariance matrix C with elements $C_{ij}$ is defined as $$C_{ij} = \frac{1}{K} \sum_{k=1}^{K} q_i^k q_j^k. \quad \text{Eq. (10)}$$

If the original coefficients $f_j(\omega)$ are independent, the off-diagonal terms of the covariance matrix will be zero. When the $f_j(\omega)$ values are independent, the flow proceeds to block 1056 where the generation of the continuous mathematical model of the common feature from the probability distribution diagram is performed.

If the original coefficients are not independent (i.e., they are dependent), then the flow proceeds to block 1054 where the coefficients are decorrelated. Two exemplary approaches are described herein: (a) estimate a joint distribution for the $f_j(\omega)$, and simulated subjects are created by drawing from that joint distribution; (b) use the covariance matrix to determine a new set of basis functions, $Q_j(t)$, and new coefficients, $s_i^k$, which are not correlated (the covariance is zero). The advantage of the former approach includes fewer required data, is computationally simpler, is an optimal expansion, and can provide powerful insight into the behavior of the feature. This approach is closely related to both the principal component method (PCM) and the method of factor analysis and is a central feature of the K-L decomposition. After the new, uncorrelated coefficients $s_j(\omega)$ are determined, it is much easier to estimate their joint distribution and draw from that distribution to create simulated subjects. Additionally, under some conditions, the new coefficients will also be independent.

The latter approach is accomplished as follows: since the covariance matrix is real, symmetric, and nonnegative, it has J+1 real eigenvalues $\lambda_j$ (with $\lambda_j \geq 0$) and J+1 orthonormal eigenvectors $\psi^j$. The eigenvectors and eigenvalues have two important properties. First, multiplying an eigenvector by the matrix from which it was derived reproduces the eigenvector scaled by the eigenvalue. Thus, $$\sum_{l=0}^{J} C_{jl} \psi_l^n = \lambda_n \psi_j^n, (j = 0 \ldots J, n = 0 \ldots J). \quad \text{Eq. (11)}$$

Second, the eigenvectors are orthonormal, $$\sum_{j=0}^{J} \psi_j^n \psi_j^l = \delta_{nl}, \quad \text{Eq. (12)}$$

where $\delta_{nl}=0$ if $n \neq l$, and $\delta_{nl}=1$ if $n=l$. Moreover, the eigenvectors span the space so that any vector can be represented as the sum of coefficients times the eigenvectors.

Using the eigenvectors of the covariance matrix, it is possible to calculate new coefficients and basis vectors for expansion of the trajectory that have the desired property that the coefficients are uncorrelated. The first step in this calculation is to expand the coefficients $q_j^k$ in terms of the eigenvectors and new coefficients $s_i^k$, $$q_j^k = \sum_{i=0}^{J} s_i^k \psi_j^i. \quad \text{Eq. (13)}$$

Eq. (13) is then used to solve for the $s_i^k$ in terms of the $q_j^k$ Multiplying each side by the nth eigenvector and summing over its elements yields $$\sum_{j=0}^{J} q_j^k \psi_j^n = \sum_{j=0}^{J} \sum_{i=0}^{J} s_i^k \psi_j^i \psi_j^n. \quad \text{Eq. (14)}$$

But by equation (12) and the orthogonality of the eigenvectors, $$\sum_{j=0}^{J} \sum_{i=0}^{J} s_i^k \psi_j^i \psi_j^n = s_n^k. \quad \text{Eq. (15)}$$

This equation defines the new coefficients in terms of the $q_j^k$ and the eigenvectors; the new coefficients are a linear combination of the old coefficients and are weighted by the elements of the corresponding eigenvectors. Thus, for the $n^{th}$ new coefficient, we obtain $$s_n^k = \sum_{j=0}^{J} q_j^k \psi_j^n. \qquad \text{Eq. (16)}$$

Similarly, we can define new basis vectors $Q_j(t)$ as linear combinations of the old basis vectors weighted by the elements of the eigenvectors. That is, $$Q_n(t) = \sum_{j=0}^{J} \psi_j^n P_j(t). \qquad \text{Eq. (17)}$$

Using Eq. (16) it can be verified that the coefficients $s_j(\omega)$ and $s_n(\omega)$ are not correlated. Thus, $$\langle s_j(\omega) s_n(\omega) \rangle = 1/K \sum_{k=1}^{K} \left( \sum_{i=0}^{J} q_i^k \psi_i^j \right) \left( \sum_{l=0}^{J} q_l^k \psi_l^n \right) \qquad \text{Eq. (18)}$$

$$= \sum_{i=0}^{J} \sum_{l=0}^{J} C_{il} \psi_i^j \psi_l^n = \sum_{i=0}^{J} \lambda_n \psi_i^j \psi_i^n = \lambda_n \delta_{jn}. \qquad \text{Eq. (19)}$$

Further, by substituting the new coefficients and basis functions, we can verify that these new coefficients and basis functions satisfy the original equation for the trajectory of the feature. Substituting Eq. (13) in equation (9) thus yields $$F^k(t) = \langle F(t) \rangle + \sum_{j=0}^{J} \sum_{l=0}^{J} s_l^k \psi_j^l P_j(t), \qquad \text{Eq. (20)}$$

and substituting equation (17) in equation (20) yields $$F^k(t) = \langle F(t) \rangle + \sum_{l=0}^{J} s_l^k Q_l(t). \qquad \text{Eq. (21)}$$

Starting from an arbitrary set of basis functions $P_j(t)$, this method can be used to derive a set of basis functions $Q_j(t)$, which cause the trajectories of real persons to best fit the observed data (i.e., passing through all observed points), but for which the coefficients, $s_j(\omega)$, are uncorrelated.

This method of expansion has many advantages. First, it corrects for first-order correlations. If the random process is Gaussian, then correcting for first-order correlations corrects for all higher order correlations and consequently makes the random variables $s_j(\omega)$ independent. Although assuming a Gaussian distribution is frequently reasonable, the method does not correct for higher order correlations. If higher order correlations are found to be important, then forming the joint distribution of the $s_j(\omega)$ may still be necessary. Even in this case, however, forming these joint distributions from equation (21) will still be easier because the first-order correlations will have been removed.

A second advantage of this method is that it provides insight into the nature of the trajectory of the feature. The K-L expansion can be optimal if the expansion in Eq. (2) is truncated at the $m^{th}$ term, the mean square error is smallest if the basis functions are the $Q_j(t)$ and the coefficients of the expansion are the $s_j^k$ as derived above. By exploring the rate at which the expansion converges when different basis functions are used and by exploring the components of the expansion's trajectory, not only can we learn about the biology of the feature but the new basis functions are likely to converge faster in the sense that fewer terms are needed to get a good fit of the data. This event can provide information about the minimum number of observations needed to formulate an accurate description of the feature's trajectory: the number of data points needed is equivalent to the number of expansion terms which have important coefficients. For example, if the data are well fitted by using only two terms in the expansion, only two data points will be needed to fit the entire function. This fact is of importance for future data collection.

The importance of each term in the expansion is assessed by examining the size of the eigenvalues $\lambda_n$. This process is similar to factor analysis. The covariance matrix has diagonal elements $\sigma_n^2$, where $$\sigma_n^2 = 1/K \sum_{k=1}^{K} (q_n^k)^2.$$

The sum of the diagonal elements of C is $$\sigma^2 = \sum_{n=1}^{J} \sigma_n^2.$$

This sum is conserved in diagonalization, so the sum of the eigenvalues is also $\sigma^2$. Just as in the factor analysis, the size of each eigenvalue represents the importance of each term in the expansion of the process, with the terms with the largest eigenvalues contributing the most to the convergence of the series. Consequently, the number of terms in the expansion can be reduced by keeping only those which have the largest eigenvalues. One frequently used method involves ordering the eigenvalues by size, calculating their sum, and retaining the first m eigenvalues such that $$\sum_{i=0}^{i=m} \lambda_i \geq Frac * \sigma^2,$$

where Frac is the percentage of the original variance the reduced eigenvector set will reproduce. In an exemplary embodiment, Frac is chosen to be substantially close to 0.9. Standard (but nonetheless empirical) methods of choosing the number of eigenvalues to retain in the factor analysis method are well known in the art and not described here.

Thus, the Fourier expansion with the K-L decomposition produces a new set of coefficients which are easier to use because they are uncorrelated (and perhaps independent). If higher order correlations exist, the K-L procedure makes finding the joint distribution of the coefficients easier. In addition, because the expansion is optimal, fewer terms in the series may be needed to adequately represent the random process. The K-L procedure also enables identification of terms to be retained.

Finally, the flow culminates at block 1056 where it is now appropriate to create new simulated subjects by drawing values from the distributions of the random variables for the coefficients and using these values in Eq. (3) to derive simulated trajectories for as many subjects as desired.

Determining distribution of data samples from a set of samples ($s_{ij}^k$) is a standard problem which is often addressed using maximum likelihood techniques. First, the application of this technique for a feature which does not depend on another feature is described, then to include dependence on other features.

An estimate of the parameters $\vec{\Theta}^{ij}$ is obtained by maximizing the likelihood as a function of the parameters $\theta_1^{ij}, \theta_2^{ij}, \ldots \theta_N^{ij}$ The following Example 2 is provided to further illustrate the above-described decorrelation workings of the present invention in conjunction with and referencing the exemplary data provided in Example 1 above:

To decorrelate the calculated $f_j^k$ Example 1, first the average value of the $f_j^k$ is removed from the distribution of each $f_j$ and then the correlation matrix is formed of the resulting coefficients. This matrix is denoted as $C_{ij}$ and an example of matrix for this set of coefficients as calculated in Example 1 is shown in Table 1 below.

TABLE 1

Correlation Matrix $C_{ij}$
Correlation Matrix---Row/column

| | 1 | 2 | 3 | 4 | 5 | 6 | 7 |
|---|---|---|---|---|---|---|---|
| 1 | 125 0011 | −1125 0165 | 5250 05775 | −10500 077 | 9843.793313 | −4331.258663 | 721.875 |
| 2 | −1125 0165 | 22125 2475 | −110250 8663 | 220501 155 | −206719 3997 | 90956 37994 | −15159 375 |
| 3 | 5250.05775 | −110250 8663 | 551253.0319 | −1102504.043 | 1033596 024 | −454781 7048 | 75796 875 |
| 4 | −10500.077 | 220501.155 | −1102504.043 | 2205005.39 | −2067190 532 | 909563 1064 | −151593.75 |
| 5 | 9843 79331 | −206719 3997 | 1033596 024 | −2067190 532 | 1937989 987 | −852715.1848 | 142119 1406 |
| 6 | −4331.2587 | 90956 37994 | −454781 7048 | 909563 1064 | −852715 1848 | 375194 5995 | −62532.42188 |
| 7 | 721 875 | −15159 375 | 75796 875 | −151593 75 | 142119.1406 | −62532 42188 | 10422 07031 |

Designating the samples as $s_{ij}^k$, where k represents the $k^{th}$ individual, j represents the $j^{th}$ term in the expansion, and i represents the $i^{th}$ feature, the probability distribution of the random variable, $s_{ij}(\omega)$ from which the samples were obtained is denoted as $\rho_{ij}$ and is characterized by a small number of parameters:

$$\rho_{ij}(x,\theta_1^{ij},\theta_2^{ij},\ldots \theta_N^{ij})dx = \rho_{ij}(x, \vec{\Theta}^{ij})dx = P(x<s_{ij}(\omega)<x+dx) \quad \text{Eq. (22).}$$

P( . . . ) is the probability that the random variable $s_{ij}(\omega)$ lies in the range between x and x+dx. $\vec{\Theta}^{ij}=\{\theta_n^{ij}, n=1\ldots N\}$ are the parameters of the distribution of $s_{ij}(\omega)$, a distribution to be determined. The probability of obtaining the samples $s_{ij}^k$ is the likelihood and is related to the distribution $\rho_{ij}$ and to the samples $s_{ij}^k$ by the likelihood function $$L(\vec{\Theta}^{ij}, s_{ij}^1, s_{ij}^2, \ldots s_{ij}^K) = \prod_{k=1}^{K} \rho_{ij}(s_{ij}^k, \vec{\Theta}^{ij}). \quad \text{Eq. (23)}$$

If the $f_j^k$ s had not been correlated, the numbers along the diagonal path of (1,1) to (7, 7) in the correlation matrix of Table 1 would have had a large numerical differential with other numbers in the table, and further processing would have then been unnecessary.

Since the $f_j^k$ s in Table 1 are correlated, the eigenvalues and eigenvectors of $C_{ij}$ matrix must be found. As described above, the eigenvectors are used to produce a new set of basis functions $Q_j(t)$, and a new set of coefficients $s_j^k$. In the basis functions determined by the $Q_j(t)$, the correlation function of the new coefficients $s_j^k$ is diagonal (i.e. uncorrelated). The eigenvectors are then used to determine which of the new basis functions is most important in expanding the trajectories. The new expansion is desireable in a number of ways as described above.

Table 2 shows the eigenvalues for the $C_{ij}$ matrix of Table 1.

TABLE 2

Eigenvalues of the Correlation matrix

| Eigenvalues | 5101964.28 | 149.6971869 | 1.348395025 | 1.69187E−10 | 6.2168E−11 | −1.59923E−12 | −6.77766E−12 |
|---|---|---|---|---|---|---|---|

Since there are seven dimensions in the matrix, there are seven eigenvalues. As shown, however, only the left two of the eigenvalues are large and the others are very close to zero. It should be noted that since the eigenvectors and eigenvalues are determined numerically, the results may have some negligible error caused by numerical approximations and rounding. Since only two of the eigenvalues are not close to zero, only two functions are necessary to reproduce the statistics of the space of trajectories. Table 3 below shows the eigenvectors of the matrix $C_{ij}$ which are used to determine the new basis expansion functions.

TABLE 3

Normalized Eigenvectors of the Correlation matrix $C_{ij}$
Normalized Eigenvectors--Row/column

|   | 1 | 2 | 3 | 4 | 5 | 6 | 7 |
|---|---|---|---|---|---|---|---|
| 1 | −0 0031315 | 0 707579343 | 0 120412793 | 0 03173556 | −0 199411047 | 0 079083239 | 0 661661814 |
| 2 | 0 06574214 | −0.704953842 | 0.117879707 | 0.03173556 | −0.199411047 | 0 079083239 | 0.661661814 |
| 3 | −0 3287052 | −0 014859284 | −0 65134236 | −0 307175909 | 0.523826746 | 0 117478323 | 0 291431948 |
| 4 | 0.65740968 | 0.03151091 | 0 303195945 | −0.076815788 | 0 674110401 | 0 024755053 | 0 118124867 |
| 5 | −0.6163211 | −0 030885735 | 0 465370383 | 0 450935555 | 0 436023995 | −0.071430679 | 0 063739208 |
| 6 | 0.27118108 | 0.014073656 | −0 474624938 | 0 833226618 | 0 034714355 | 0 065398083 | 0 03528921 |
| 7 | −0 0451968 | −0 002412822 | 0 116584985 | 0 010887236 | −0 018142897 | 0.981681447 | −0 142173161 |

The new functions are $Q_0$, and $Q_1$ as shown below, $Q_0(y) = -0.003135 + 0.06574214y - 0.3287052*y^2 + 0.65740968*y^3 - 0.6163211*y^4 + 0.27118108*y^5 - 0.0451968*y^6$ $Q_1(y) = 0.7075793 - 0.704953842y - 0.01485928*y^2 + 0.03151091*y^3 - 0.030885735*y^4 + 0.014073656*y^5 - 0.002412822*y^6$ where y is the function (t/50) used in Example 1. Since J was set to 6, the terms in each of the $Q_0$, and $Q_1$ series also proceeds to seven.

Figure 9A:
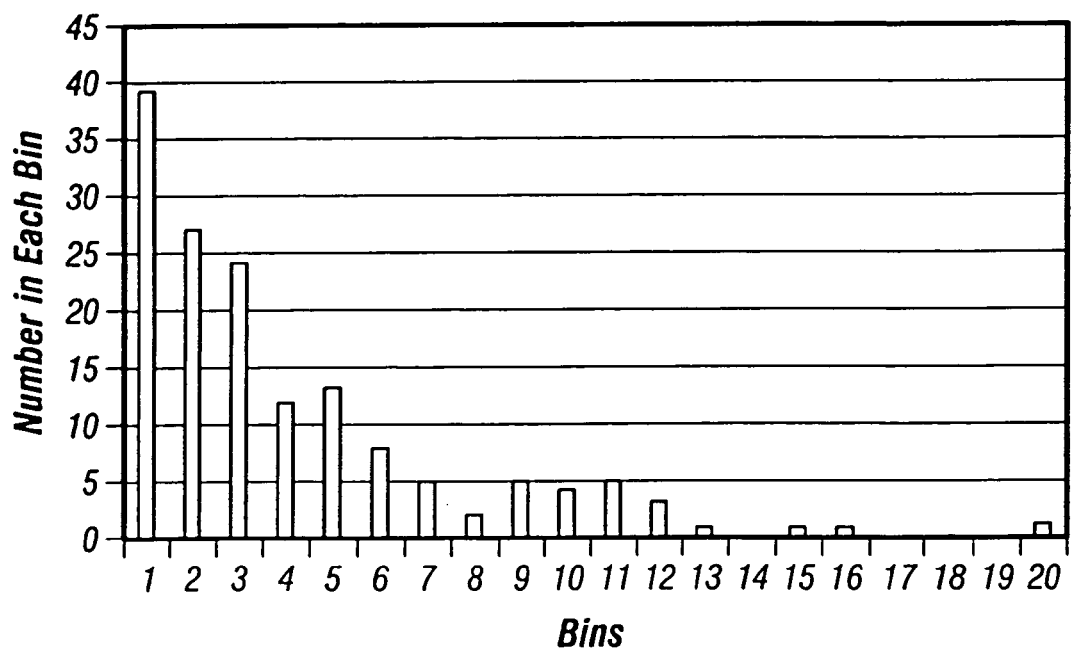
Figure 9B:
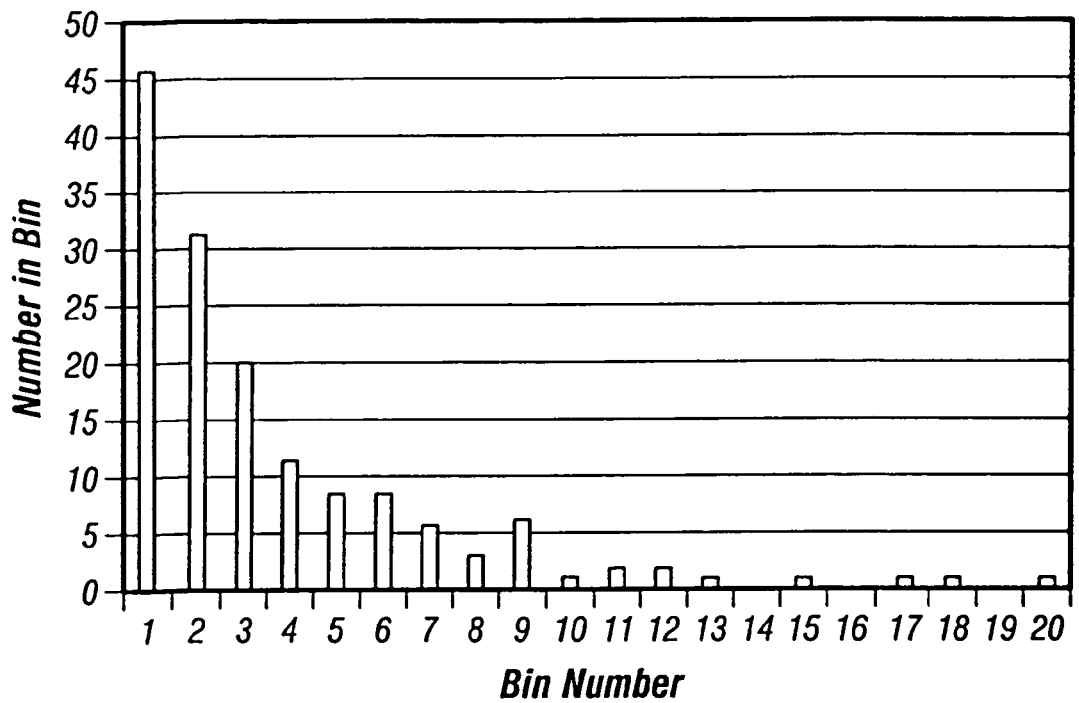
Figure 9C:
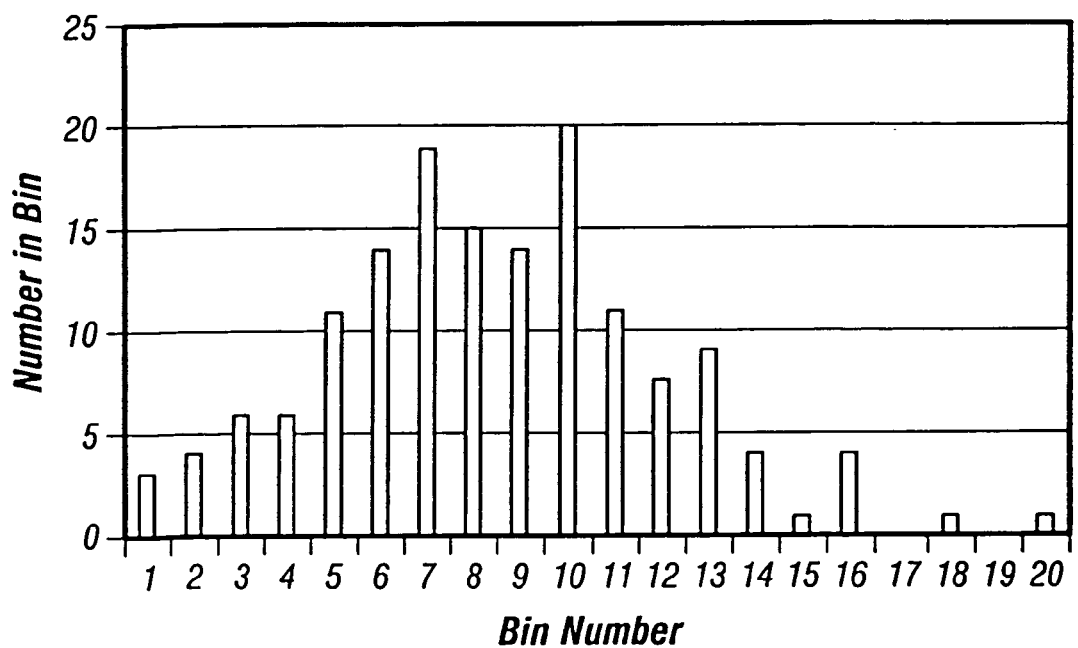

The samples for the distribution for the random variables $s_0$ and $s_1$ are shown in FIGS. 9B and 9C. The distribution for $s_0$ looks like an exponential distribution. Using maximum likelihood techniques described above, the distribution for $s_0$ is found to be $P_0(s) = \exp(-s/\lambda)/\lambda$ where $\lambda = 3513$, as shown in FIG. 9C. The distribution for $s_1$ resembles a normal distribution. Also, using maximum likelihood techniques, the distribution for $s_1$ is found to be normal with standard deviation 12.4, as shown in FIG. 9C.

In an exemplary embodiment, the presented mathematical model may be used in cases of incomplete data, such as when person specific data on values of the feature exist at several times (but not necessarily at the same times for each person). This situation is a realistic one for many problems today and constitutes a restriction shared by most statistical models, such as regression models. Moreover, person specific data are likely to become far more available with increased use of automated clinical information systems.

Currently, a large class of clinical conditions exist for which the feature is difficult or practically impossible to observe and for which the only data available relate to occurrence of clinical events. For example, several large epidemiologic studies provide data on probability of heart attack for subjects of various ages, but no large studies exist on degree of occlusion of coronary arteries (because the required measurement entails use of often risky, expensive tests). In such cases, choice of approach depends on availability of data from ancillary sources on the relation between feature and clinical event. When available, data such as reports on degree of occlusion in patients who recently had a heart attack can be used to translate epidemiologic data on clinical events into estimates of values of the feature, and the process described above may then be used to complete the derivations of equations for the trajectory of the feature.

When there are no data at all on the value of a feature at the time of clinical events, a different approach may be used. In this case the method is not dependent on equations for the trajectory of the true values of the feature because such an approach is not possible if there are truly no systematic observations of the feature. Instead, the method depends on equations for an imaginary feature whose only purpose is to accurately reproduce the observed occurrence of clinical events. For this purpose, the desired feature can be assigned an arbitrary value when the event occurs. If there is more than one clinical event to be simulated, the arbitrary values should correspond to the order in which the events occur. If the events occur in different orders in different subjects, a strong likelihood exists that the events are caused by different features, and equations for each feature can be derived accordingly. Although this approach provides little information about the true value of the feature, it does provide what is needed for an accurate simulation, which is a feature that produces clinical events at rates that "statistically match" the occurrences of real clinical events.

Finally, some cases involve situations when there are no person specific data, and the only available data are aggregated over a population. For example, there may be data on the age distribution of patients diagnosed with various stages of a cancer, but no person specific data on the ages at which particular individuals pass through each stage. Of course, if there are data from other sources that relate the clinical events to the values of the feature (in this example the "stage" of the cancer), those data can be used to resolve the problem as described in the previous section. Assuming there are no such data, there are two below-described main options, depending on whether there is reason to believe that the clinical events are correlated.

Under the first option, if an assumption can be made that the clinical events are not correlated, then they can be modeled as if caused by two different features, and the modeling problem is reduced to one of the cases discussed above. If it is undesirable to assume that the events are uncorrelated, then a model is to be postulated that describes the correlation as follows: first a search is made for any data on which the presumption of correlation was based, and those data are used to develop a model. But even if no such data are available there may be plausible reasons to postulate a model. For example, an assumption can be made that some individuals have an "aggressive" form of the disease, implying that they will move through each stage relatively rapidly, whereas others may have more "indolent" cancers, implying that their disease will tend to progress more slowly. Thus if a person with an aggressive disease was in the first 10% in terms of the age at which they developed the first stage of the disease, it might be plausible to assume that they will be in the first 10% in the pace at which they progress through subsequent stages. If a specific correlation is postulated, then it is possible to convert the cross-sectional data into a set of person specific longitudinal data. At this stage, the problem is transformed into the original case and can be solved by the above described methods.

Figure 11:
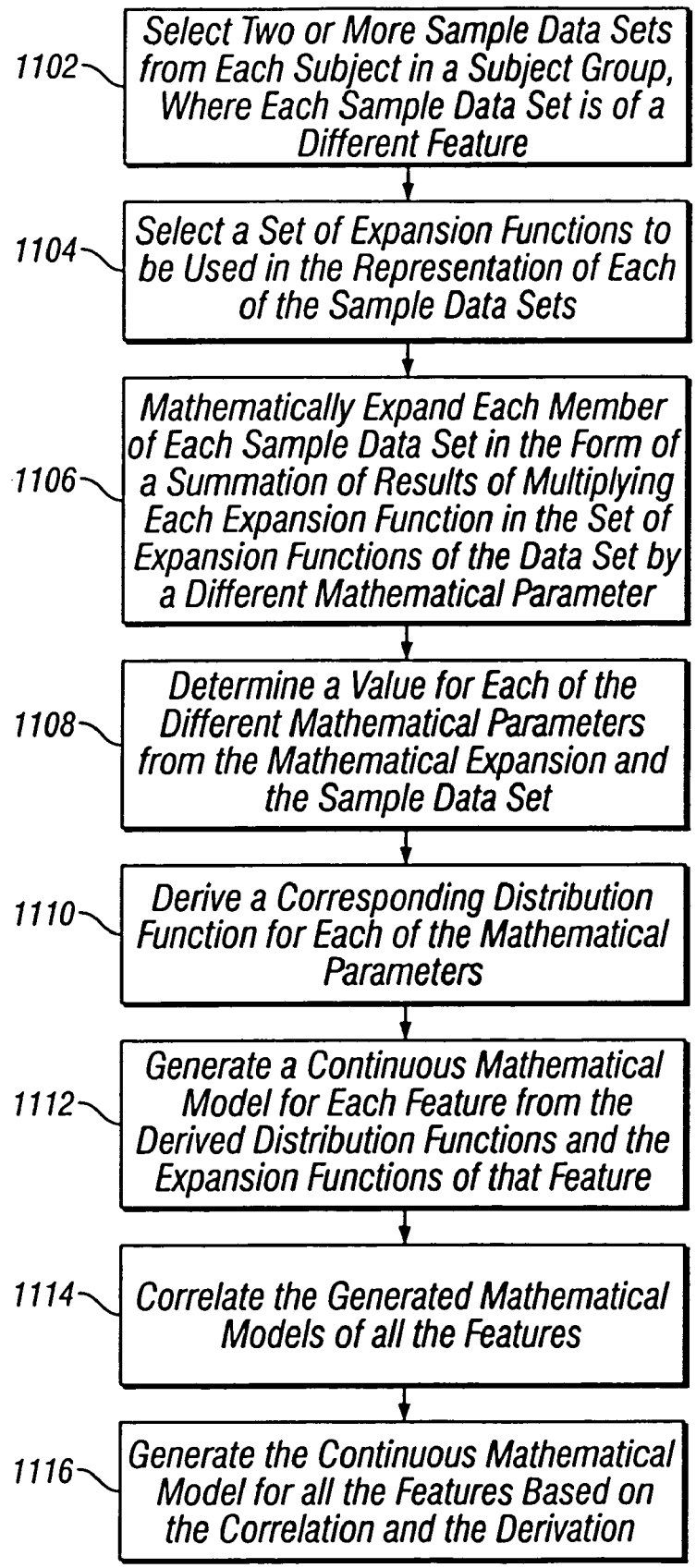
FIG. 11 is a process flow diagram illustrating a method for generating a continuous mathematical model in accordance with another embodiment of the invention.

In another embodiment shown in FIG. 11, the mathematical model of the present invention can be used for multiple features common to a subject group, and for generating trajectories that represent the interdependence of these common features, such as plotting a coronary occlusion as function of blood pressure or cholesterol level. As shown in the flow diagram of FIG. 11, generating the continuous mathematical model of two features starts at block 1102 where two or more sample data sets of different features from each subject in the subject group are selected. Next, at block 1104, a set of expansion functions to be used in the representation of the each of the sample data sets is also selected. At block 1106, the selections made in blocks 1102 and 1104 are used to mathematically expand each member of each sample data set in the form of a summation of the results of multiplying each of the expansion functions in the set of expansion functions of the data set by a different mathematical parameter. Next, at block 1108, a value for each of the different mathematical parameters are determined from the mathematical expansion of block 1106. Next, at block 1110, a corresponding distribution function for each of the mathematical parameters is derived based on the values determined in block 1108. Next, at block 1112, a continuous mathematical model for each of the features selected in block 1102 is generated from the derived distribution functions of block 1110 and the expansion functions of block 1106. Next, at block 1114, the mathematical models for each of the features generated in block 1112 are correlated. Finally, at block 1116, a continuous mathematical model is generated based on the correlation results of block 1114, that accounts for all the features selected at block 1102. Many of the details of operations of this embodiment of the present invention, particularly those in blocks 1102 to 1112 were discussed in conjunction with FIG. 1 or can be readily understood therefrom. The following detailed description is therefore focused primarily on the correlating operations performed in block 1114 of FIG. 11.

At block 1114, the equations for multiple features depend on the extent to which features are independent such that they depend only on time (e.g., a person's age) and do not depend on other features or other factors that may vary across individual persons. It should be apparent that for features that are independent as such and depend only on an individual's age, the methods already described can be used to derive equations for as many such features as desired.

The difficulties arise when the trajectory of a feature depends on other features or other risk factors. For the example of coronary artery disease, the rate of coronary artery occlusion depends not only on age but also on other features, such as cholesterol level, blood pressure level, tobacco use, and diabetes. Collectively these are referred to as "risk factors" throughout this disclosure with the understanding that this term covers a wide range of disparate factors. Some of these factors are fixed characteristics (e.g., sex, race), some are biologic features (e.g., cholesterol), some are behaviors (e.g., smoking), some can be modified by interventions while some cannot. Fortunately, the method for incorporating risk factors in the trajectory of a feature works for all types of risk factors. Explained in greater detail below is incorporating a dependence on features, with the understanding that the method can easily incorporate dependence on other risk factors.

First, it should be noted that the dependence of one feature on other features is already incorporated in the data, and therefore is incorporated in the coefficients and basis functions estimated for each individual in Eqs (3), (9), or (21). The task then, is to separate that dependence and to represent it explicitly in the coefficients or basis functions of the equations for the trajectory of the feature. This is needed if a general model is to be developed that can be used to analyze interventions, not only in clones of the original population, but also in a wide variety of other populations that will have different distributions of risk factors.

The separation of the dependence on other features requires care, because the data for estimating the equations for a feature contain all the dependence of the feature on age. But the data are not separated into the dependence of the feature as a function of age, at a fixed value of another feature, or the dependence of the feature as a function of another feature, at a fixed age.

The dependence can be represented either in the coefficients or in the basis functions. In the Fourier expansion approach, the dependence is represented in the coefficients. Described herein are methods to determine the distributions of the coefficients from the available data, when the features are related in a Fourier expansion and one feature depends on another. In the Hybrid expansion approach, the dependence is represented in the basis functions or in both the basis functions and the coefficients. Using the Hybrid approach facilitates inclusion of the dependence of one feature on another because the independent features (such as total cholesterol level in the expansion of the coronary artery occlusion) are explicitly separated out and included in the basis functions. The trade off is that the Hybrid expansion is not guaranteed to converge and the equations for determining the coefficients for the hybrid expansion may be ill-conditioned.

Using the same notation as in Eq. (22) and (23), the distributions of the coefficients of the random process for the $i^{th}$ feature, $F_i(\omega,t)$ can be considered to be conditional on the coefficients of the random processes of other features. To allow the distributions to be conditional, we represent the $\Theta^{ij}$ as functions of the other coefficients, i.e., $$P(x<s_{ij}(\omega)<x+dx|\hat{s}_i(\omega)=\hat{x}_i)=\rho_{ij}(x,\vec{\Theta}^{ij}(\hat{x}_i)) \qquad \text{Eq. (24)}.$$

The set $\hat{s}(\omega)$ represents the coefficients of all features other than feature i (i.e., all $s_{i'j'}(\omega)$ for $i' \neq i$ and all j'), and $\hat{x}_i$ represents the set of all x except for $x_i$. The $\vec{\Theta}^{ij}(\hat{x})$ may be chosen to be a function of the coefficients $\hat{x}_i$ in many different ways. One common choice is using an expansion linear in the coefficients, e.g., $$\vec{\Theta}^{ij}(\hat{x}_i) = \vec{\Theta}^{ij}\left(\vec{\beta}_0^{ij} + \sum_{i' \neq i, \text{ all } j'}^{I} \vec{\beta}_{i'j'}^{ij} x_{i'j'}\right) \qquad \text{Eq. (25)}$$

and another alternative is using an expansion which depends on some powers of the coefficients, e.g., $$\vec{\Theta}^{ij}(\hat{x}_i) = \vec{\Theta}^{ij}\left(\vec{\gamma}_0^{ij} + \sum_{i' \neq i, \text{ all } j'}^{I} \sum_{l=0}^{L} \vec{\gamma}_{i'j'l}^{ij} (x_{i'j'})^l\right) \qquad \text{Eq. (26)}$$

In general, $\vec{\Theta}^{ij}(\hat{x})$ can be represented as $$\vec{\Theta}^{ij}(\hat{x}_i) = \vec{\Theta}^{ij}(\vec{\beta}_0^{ij} H^{ij}(\hat{x})) \qquad \text{Eq. (27)},$$

where $H(\hat{x})$ can be either of the forms shown in equations (25) or (26) or some other function of the $\hat{x}$, e.g., $$H^{ij}(\hat{x}) = \exp\left(\sum_{i' \neq i, \text{ all } j'}^{I} \sum_{l=0}^{L} \vec{\gamma}_{i'j'l}^{ij}(x_{i'j'})^l\right). \qquad \text{Eq. (28)}$$

The likelihood of obtaining all the sample values $s_{ij}^k$ for all the individuals $k=1 \ldots K$, and all the features i, and all the coefficients j for the expression in equation 27 is given by the equation $$L(\vec{B}, \vec{s}) = \prod_{k=1, i, \text{ all } j}^{K, I} \rho_{ij}\left(s_{ij}^k, \vec{\Theta}^{ij}(\hat{x}_i)\right), \qquad \text{Eq. (29)}$$

where $\vec{B}$ is the vector of all coefficients in equation (25) $\vec{B} = \{\vec{\beta}_0^{ij} \vec{\beta}_{ij'}^{ij}\}$ or in Eq. (26) $\vec{B} = \{\vec{\gamma}_0^{ij}, \vec{\gamma}_{ij'}^{ij}\}$ and where $\vec{s}$ represents the set of all coefficients obtained by observations on all subjects. The $\vec{B}$ coefficients are determined by maximizing the likelihood in Eq. (29). These coefficients determine the probability distribution function for the coefficients of each term of each feature. Notice that for the form given in Eq. (28), the Fourier expansion can be transformed to the hybrid expansion by incorporating the coefficients of some features into the basis functions.

After functions have been derived for the natural histories of features, linking features to events is a fairly straightforward process. First, biologic events are represented by the values of features. Tests can be applied to measure a feature at any time, and the raw result of the test is read directly from the value of the feature. Uncertainty, random error, and systematic error in tests are easy to include.

For clinical events, for example, if the feature was observed through the clinical event the trajectory will automatically reproduce the occurrence as required. Otherwise, it is necessary to describe or model how the clinical event is linked to the feature. The appropriate model will depend on the data available. For example, a standard medical text suggests that angina pain tends to occur when degree of coronary artery occlusion approaches 70%. Clinical events can also be defined as more complex functions of a feature. For example, rapid weight change in a patient with congestive heart failure is an indication to regulate dose of diuretics. Because values of all features are continuously available through equations for trajectories, it is a relatively easy task to define models which determine occurrence of clinical events on the basis of evidence or customary practice.

Effects of health interventions can also be modeled either as a change in value of a feature, as the rate of change of a feature, or as a combination of both types of change. The choice and the exact model depend on the intervention and on the available data.

Based on the above disclosure, the present invention offers several advantages over the prior art: the mathematical model presented herein is a true simulation with a highly detailed one-to-one correspondence between objects in the model and objects in the real world. The level of detail allows for detailed description of events and features, such as occlusion of specific coronary arteries at specific areas along the artery or propensity of a particular physician to follow a particular guideline. The presented model is also truly continuous and can be applied in representation of practically any event occurring to any subject at any time. This characteristic is particularly important because many decisions involve timing such as in health care where the factor such as how frequently to monitor a patient, when to initiate or modify a treatment, how frequently to schedule follow up visits, how long to wait before taking some action all play an important role in the decision making process.

In an exemplary embodiment, the invention may be implemented using object-oriented programming with the major classes of objects in the model to include subjects such as members, patients, facilities, personnel, interventions, equipment, supplies, records, policies, and budgets. Those of ordinary skill in the art will now realize that the invention may also be implemented using any appropriate programming techniques.

While embodiments and applications of this invention have been shown and described, it would be apparent to those skilled in the art having the benefit of this disclosure that many more modifications than mentioned above are possible without departing from the inventive concepts herein. The invention, therefore, is not to be restricted except in the spirit of the appended claims.

What is claimed is:

1. A computer-implemented method for generating a continuous mathematical model of a feature common to subjects in a subject group, wherein the subjects are biological subjects and the feature is a biological feature, the method comprising:

determining a plurality of sample data sets corresponding to at least one physiological characteristic of the subjects in the subject group;

determining, from the sample data sets, a plurality of values for one or more mathematical parameters corresponding to one or more basis functions for the continuous mathematical model;

determining, from the values for the one or more mathematical parameters, one or more distribution-function parameters for specifying one or more distribution functions for the one or more mathematical parameters, wherein a summation of the one or more basis functions multiplied by sampled values of the one or more distribution functions provides the continuous mathematical model of the feature;

simulating the feature by generating sampled values of the one or more distribution functions by computer;

calculating at least one statistical property of the simulated feature for characterizing the at least one physiological characteristic of the subjects in the subject group; and saving the at least one statistical property of the simulated feature.

2. A method according to claim 1, wherein determining the sample data sets includes receiving the sample data sets from an external data source and storing the sample data sets in a computer memory.

3. A method according to claim 2, wherein determining the sample data sets includes measuring values for the feature and storing the values for the feature in the external data source.

4. A method according to claim 3, wherein measuring the values for the feature includes measuring values of blood pressure for the subjects in the subject group.

5. A method according to claim 1, wherein determining the values for the one or more mathematical parameters includes:
   determining initial values for the one or more mathematical parameters according to an optimization criterion;
   separating the initial values into bins with corresponding bin ranges.

6. A method according to claim 1, wherein determining the values for the one or more mathematical parameters includes calculating the values for the one or more mathematical parameters from the sample data sets according to an optimization criterion.

7. A method according to claim 1, wherein determining the one or more distribution-function parameters includes calculating the one or more distribution-function parameters from the values for the one or more mathematical parameters according to an optimization criterion.

8. A method according to claim 1, further comprising:
   displaying the at least one statistical property of the simulated feature.

9. A method according to claim 1, wherein determining the values for the one or more mathematical parameters corresponding to the one or more basis functions includes:
   selecting a plurality of initial basis functions;
   determining a plurality of values for a plurality of mathematical parameters corresponding to the initial basis functions;
   determining, from the values for the mathematical parameters corresponding to the initial basis functions, a correlation matrix for the initial basis functions; and
   determining, from the correlation matrix, the one or more basis functions according to a de-correlation criterion.

10. A method according to claim 1, wherein the feature is a first feature selected from a plurality of features that includes a second feature, and the method further comprises:
    determining, from the sample data sets, a plurality of values for one or more second mathematical parameters corresponding to one or more second basis functions for a continuous mathematical model of the second feature; and
    determining, from the values for the one or more second mathematical parameters, one or more second distribution-function parameters, wherein
      values for the features other than the second feature and values for the one or more second distribution-function parameters specify the one or more second distribution functions for the one or more second mathematical parameters, and
      a summation of the one or more second basis functions multiplied by sampled values of the one or more second distribution functions provides the continuous mathematical model of the second feature.

11. A method according to claim 10, further comprising:
    simulating the second feature by computer, for given values of the features other than the second feature, by generating sampled values of the one or more second distribution functions;
    calculating at least one statistical property of the simulated second feature for characterizing the at least one physiological characteristic of the subjects in the subject group; and
    saving the at least one statistical property of the simulated second feature.

12. A method according to claim 1, wherein the one or more basis functions include a single basis function and the summation includes a single term.

13. A method according to claim 1, wherein the one or more basis functions include a plurality of orthogonal functions over a continuous interval.

14. A method according to claim 1, wherein the one or more basis functions include one or more hybrid functions that characterize features common to the subject group over a continuous interval.

15. A method according to claim 14, wherein
   the continuous mathematical model of the feature includes a model for occlusion of a coronary artery over the continuous interval, and
   the one or more hybrid functions include a first function for blood pressure and a second function for cholesterol level.

16. A method according to claim 15, wherein the one or more hybrid functions include a third function for a product of the blood pressure and the cholesterol level.

17. A method according to claim 1, wherein a computer determines the values for the one or more mathematical parameters and the one or more distribution-function parameters.

18. A method according to claim 1, wherein feature is selected from the group consisting of blood pressure, cholesterol levels, bone mineral density, patency of a coronary artery, heart electrical potentials, contractility of myocardium, cardiac output, visual acuity, serum potassium level, observations for a rash, diameter of a coronary artery, and cancer spread measurements.

19. A method according to claim 1, wherein the one or more distribution functions include at least one normal distribution function and the one or more distribution-function parameters include at least one corresponding standard-deviation parameter.

20. An apparatus for generating a continuous mathematical model of a feature common to subjects in a subject group, wherein the subjects are biological subjects and the feature is a biological feature, the apparatus comprising a computer for executing computer instructions, wherein the computer includes computer instructions for:
   determining a plurality of sample data sets corresponding to at least one physiological characteristic of the subjects in the subject group;
   determining, from the sample data sets, a plurality of values for one or more mathematical parameters corresponding to one or more basis functions for the continuous mathematical model;
   determining, from the values for the one or more mathematical parameters, one or more distribution-function parameters for specifying one or more distribution functions for the one or more mathematical parameters, wherein a summation of the one or more basis functions multiplied by sampled values of the one or more distribution functions provides the continuous mathematical model of the feature;
   simulating the feature by generating sampled values of the one or more distribution functions by computer;
   calculating at least one statistical property of the simulated feature for characterizing the at least one physiological characteristic of the subjects in the subject group; and
   saving the at least one statistical property of the simulated feature.

21. An apparatus according to claim 20, wherein determining the sample data sets includes receiving the sample data sets from an external data source and storing the sample data sets in a computer memory.

22. An apparatus according to claim 21, wherein the sample data sets include values of blood pressure for the subjects in the subject group.

23. An apparatus according to claim 20, wherein determining the values for the one or more mathematical parameters includes:
   determining initial values for the one or more mathematical parameters according to an optimization criterion; and
   separating the initial values into bins with corresponding bin ranges.

24. An apparatus according to claim 20, wherein determining the values for the one or more mathematical parameters includes calculating the values for the one or more mathematical parameters from the sample data sets according to an optimization criterion.

25. An apparatus according to claim 20, wherein determining the one or more distribution-function parameters includes calculating the one or more distribution-function parameters from the values for the one or more mathematical parameters according to an optimization criterion.

26. An apparatus according to claim 20, wherein the computer further includes computer instructions for:
   displaying the at least one statistical property of the simulated feature.

27. An apparatus according to claim 20, wherein determining the values for the one or more mathematical parameters corresponding to the one or more basis functions includes:
   selecting a plurality of initial basis functions;
   determining a plurality of values for a plurality of mathematical parameters corresponding to the initial basis functions;
   determining, from the values for the mathematical parameters corresponding to the initial basis functions, a correlation matrix for the initial basis functions; and
   determining, from the correlation matrix, the one or more basis functions according to a de-correlation criterion.

28. An apparatus according to claim 20, wherein the feature is a first feature selected from a plurality of features that includes a second feature, and the computer further includes computer instructions for:
   determining, from the sample data sets, a plurality of values for one or more second mathematical parameters corresponding to one or more second basis functions for a continuous mathematical model of the second feature; and
   determining, from the values for the one or more second mathematical parameters, one or more second distribution-function parameters, wherein
      values for the features other than the second feature and values for the one or more second distribution-function parameters specify the one or more second distribution functions for the one or more second mathematical parameters, and
      a summation of the one or more second basis functions multiplied by sampled values of the one or more second distribution functions provides the continuous mathematical model of the second feature.

29. An apparatus according to claim 28, wherein the computer further includes computer instructions for:
   simulating the second feature by computer, for given values of the features other than the second feature, by generating sampled values of the one or more second distribution functions;
   calculating at least one statistical property of the simulated second feature for characterizing the at least one physiological characteristic of the subjects in the subject group; and
   saving the at least one statistical property of the simulated second feature.

30. An apparatus according to claim 20, wherein the one or more basis functions include a single basis function and the summation includes a single term.

31. An apparatus according to claim 20, wherein the one or more basis functions include a plurality of orthogonal functions over a continuous interval.

32. An apparatus according to claim 20, wherein the one or more basis functions include one or more hybrid functions that characterize features common to the subject group over a continuous interval.

33. An apparatus according to claim 32, wherein
   the continuous mathematical model of the feature includes a model for occlusion of a coronary artery over the continuous interval, and
   the one or more hybrid functions include a first function for blood pressure and a second function for cholesterol level.

34. An apparatus according to claim 33, wherein the one or more hybrid functions include a third function for a product of the blood pressure and the cholesterol level.

35. An apparatus according to claim 20, wherein the feature is selected from the group consisting of blood pressure, cholesterol levels, bone mineral density, patency of a coronary artery, heart electrical potentials, contractility of myocardium, cardiac output, visual acuity, serum potassium level, observations for a rash, diameter of a coronary artery, and cancer spread measurements.

36. An apparatus according to claim 20, wherein the one or more distribution functions include at least one normal distribution function and the one or more distribution-function parameters include at least one corresponding standard-deviation parameter.

37. A computer-readable medium that stores a computer program for generating a continuous mathematical model of a feature common to subjects in a subject group, wherein the subjects are biological subjects and the feature is a biological feature, the computer program comprising instructions for:
   determining a plurality of sample data sets corresponding to at least one physiological characteristic of the subjects in the subject group;
   determining, from the sample data sets, a plurality of values for one or more mathematical parameters corresponding to one or more basis functions for the continuous mathematical model;
   determining, from the values for the one or more mathematical parameters, one or more distribution-function parameters for specifying one or more distribution functions for the one or more mathematical parameters, wherein a summation of the one or more basis functions multiplied by sampled values of the one or more distribution functions provides the continuous mathematical model of the feature;
   simulating the feature by generating sampled values of the one or more distribution functions by computer;
   calculating at least one statistical property of the simulated feature for characterizing the at least one physiological characteristic of the subjects in the subject group; and
   saving the at least one statistical property of the simulated feature.

38. A computer-readable medium according to claim 37, wherein determining the sample data sets includes receiving the sample data sets from an external data source and storing the sample data sets in a computer memory.

39. A computer-readable medium according to claim 38, wherein the sample data sets include values of blood pressure for the subjects in the subject group.

40. A computer-readable medium according to claim 37, wherein determining the values for the one or more mathematical parameters includes:
   determining initial values for the one or more mathematical parameters according to an optimization criterion; and
   separating the initial values into bins with corresponding bin ranges.

41. A computer-readable medium according to claim 37, wherein determining the values for the one or more mathematical parameters includes calculating the values for the one or more mathematical parameters from the sample data sets according to an optimization criterion.

42. A computer-readable medium according to claim 37, wherein determining the one or more distribution-function parameters includes calculating the one or more distribution-function parameters from the values for the one or more mathematical parameters according to an optimization criterion.

43. A computer-readable medium according to claim 37, wherein the computer program further comprises instructions for:
   displaying the at least one statistical property of the simulated feature.

44. A computer-readable medium according to claim 37, wherein determining the values for the one or more mathematical parameters corresponding to the one or more basis functions includes:
   selecting a plurality of initial basis functions;
   determining a plurality of values for a plurality of mathematical parameters corresponding to the initial basis functions;
   determining, from the values for the mathematical parameters corresponding to the initial basis functions, a correlation matrix for the initial basis functions; and
   determining, from the correlation matrix, the one or more basis functions according to a de-correlation criterion.

45. A computer-readable medium according to claim 37, wherein the feature is a first feature selected from a plurality of features that includes a second feature, and the computer program further comprises instructions for:
   determining, from the sample data sets, a plurality of values for one or more second mathematical parameters corresponding to one or more second basis functions for a continuous mathematical model of the second feature; and
   determining, from the values for the one or more second mathematical parameters, one or more second distribution-function parameters, wherein
      values for the features other than the second feature and values for the one or more second distribution-function parameters specify the one or more second distribution functions for the one or more second mathematical parameters, and
      a summation of the one or more second basis functions multiplied by sampled values of the one or more second distribution functions provides the continuous mathematical model of the second feature.

46. A computer-readable medium according to claim 45, wherein the computer program further comprises instructions for:
   simulating the second feature by computer, for given values of the features other than the second feature, by generating sampled values of the one or more second distribution functions;
   calculating at least one statistical property of the simulated second feature for characterizing the at least one physiological characteristic of the subjects in the subject group; and
   saving the at least one statistical property of the simulated second feature.

47. A computer-readable medium according to claim 37, wherein the one or more basis functions include a single basis function and the summation includes a single term.

48. A computer-readable medium according to claim 37, wherein the one or more basis functions include a plurality of orthogonal functions over a continuous interval.

49. A computer-readable medium according to claim 37, wherein the one or more basis functions include one or more hybrid functions that characterize features common to the subject group over a continuous interval.

50. A computer-readable medium according to claim 49, wherein
   the continuous mathematical model of the feature includes a model for occlusion of a coronary artery over the continuous interval, and
   the one or more hybrid functions include a first function for blood pressure and a second function for cholesterol level.

51. A computer-readable medium according to claim 50, wherein the one or more hybrid functions include a third function for a product of the blood pressure and the cholesterol level.

52. A computer-readable medium according to claim 37, wherein the feature is selected from the group consisting of blood pressure, cholesterol levels, bone mineral density, patency of a coronary artery, heart electrical potentials, contractility of myocardium, cardiac output, visual acuity, serum potassium level, observations for a rash, diameter of a coronary artery, and cancer spread measurements.

53. A computer-readable medium according to claim 37, wherein the one or more distribution functions include at least one normal distribution function and the one or more distribution-function parameters include at least one corresponding standard-deviation parameter.

* * * * *